(12) United States Patent
Covey et al.

(10) Patent No.: US 9,034,257 B2
(45) Date of Patent: May 19, 2015

(54) HIGH THROUGHPUT FLOW CYTOMETRY SYSTEM AND METHOD

(75) Inventors: Todd Covey, San Carlos, CA (US);
Adam Palazzo, San Francisco, CA (US);
Norman Purvis, Franklin, TN (US);
James Cordiero, Redwood City, CA (US); David Rosen, Mountain View, CA (US)

(73) Assignee: Nodality, Inc., South San Francisco, CA (US)

( * ) Notice: Subject to any disclaimer, the term of this patent is extended or adjusted under 35 U.S.C. 154(b) by 357 days.

(21) Appl. No.: 12/606,869

(22) Filed: Oct. 27, 2009

(65) Prior Publication Data
US 2010/0105074 A1    Apr. 29, 2010

Related U.S. Application Data

(60) Provisional application No. 61/181,211, filed on May 26, 2009, provisional application No. 61/162,598, filed on Mar. 23, 2009, provisional application No. 61/108,803, filed on Oct. 27, 2008.

(51) Int. Cl.
| | |
|---|---|
| *G01N 33/53* | (2006.01) |
| *G01N 35/10* | (2006.01) |
| *G01N 33/50* | (2006.01) |
| *G01N 35/00* | (2006.01) |
| *G01N 35/02* | (2006.01) |

(52) U.S. Cl.
CPC ............ *G01N 35/1095* (2013.01); *G01N 33/53* (2013.01); *G01N 33/5008* (2013.01); *G01N 35/00722* (2013.01); *G01N 35/028* (2013.01); *G01N 2035/00435* (2013.01); *G01N 2035/00752* (2013.01); *G01N 2035/0091* (2013.01)

(58) Field of Classification Search
USPC ........... 435/7.1, 7.2, 7.21, 7.23, 286.5, 287.1, 435/287.2, 287.3, 287.8, 288.4, 374, 375; 436/540, 546, 548, 52, 53, 54, 10, 35, 436/63, 64, 65, 172, 180; 422/50, 63, 54, 422/68.1, 81, 82, 82.05, 82.08, 521–524
See application file for complete search history.

(56) References Cited

U.S. PATENT DOCUMENTS

| | | |
|---|---|---|
| 4,700,294 A | 10/1987 | Haynes |
| 4,845,653 A | 7/1989 | Conrad et al. |
| 4,987,539 A | 1/1991 | Moore et al. |

(Continued)

FOREIGN PATENT DOCUMENTS

| | | |
|---|---|---|
| EP | 1041386 A2 | 10/2000 |
| EP | 1041386 A3 | 4/2001 |

(Continued)

OTHER PUBLICATIONS

Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.

(Continued)

*Primary Examiner* — Gail R Gabel
(74) *Attorney, Agent, or Firm* — Wilson Sonsini Goodrich & Rosati

(57) ABSTRACT

The invention provides systems, compositions, kits and methods for automated processing of biological samples and analysis using a flow cytometer.

49 Claims, 10 Drawing Sheets

(56) References Cited

U.S. PATENT DOCUMENTS

| | | | |
|---|---|---|---|
| 5,023,080 A | 6/1991 | Gupta | |
| 5,079,005 A | 1/1992 | Gupta | |
| 5,122,453 A | 6/1992 | Martin et al. | |
| 5,224,058 A | 6/1993 | Mickaels et al. | |
| 5,314,825 A | 5/1994 | Weyrauch et al. | |
| 5,348,705 A | 9/1994 | Koreyasu et al. | |
| 5,358,691 A | 10/1994 | Clark et al. | |
| 5,422,277 A | 6/1995 | Connelly et al. | |
| 5,451,505 A | 9/1995 | Dollinger | |
| 5,597,688 A | 1/1997 | Connelly et al. | |
| 5,627,040 A | 5/1997 | Bierre et al. | |
| 5,739,000 A | 4/1998 | Bierre et al. | |
| 5,812,419 A | 9/1998 | Chupp et al. | |
| 5,968,731 A * | 10/1999 | Layne et al. | 435/5 |
| 5,968,738 A | 10/1999 | Anderson et al. | |
| 6,004,572 A | 12/1999 | Harvan et al. | |
| 6,014,904 A | 1/2000 | Lock | |
| 6,121,048 A | 9/2000 | Zaffaroni et al. | |
| 6,178,382 B1 | 1/2001 | Roederer et al. | |
| 6,242,209 B1 | 6/2001 | Ransom et al. | |
| 6,374,683 B1 | 4/2002 | Hunicke-Smith et al. | |
| 6,387,328 B1 | 5/2002 | Berndtsson | |
| 6,399,365 B2 | 6/2002 | Besemer et al. | |
| 6,495,333 B1 | 12/2002 | Willmann et al. | |
| 6,520,618 B2 | 2/2003 | Yoshida et al. | |
| 6,733,743 B2 | 5/2004 | Jordan | |
| 6,830,936 B2 | 12/2004 | Anderson et al. | |
| 6,890,487 B1 | 5/2005 | Sklar et al. | |
| 6,944,338 B2 | 9/2005 | Lock et al. | |
| 6,947,953 B2 | 9/2005 | Herzenberg et al. | |
| 6,954,722 B2 | 10/2005 | Parks et al. | |
| 7,314,595 B2 * | 1/2008 | Honkanen et al. | 422/63 |
| 7,316,897 B2 | 1/2008 | Bisconte de Saint Julien et al. | |
| 7,316,906 B2 | 1/2008 | Chiorazzi et al. | |
| 7,321,843 B2 | 1/2008 | Orfao De Matos Correia E Vale et al. | |
| 7,329,502 B2 | 2/2008 | Staudt et al. | |
| 7,368,084 B2 | 5/2008 | Sklar et al. | |
| 7,393,656 B2 | 7/2008 | Perez et al. | |
| 7,555,492 B2 | 6/2009 | Herzenberg et al. | |
| 7,563,584 B2 * | 7/2009 | Perez et al. | 435/7.2 |
| 7,650,351 B2 | 1/2010 | Herzenberg et al. | |
| 7,695,924 B2 | 4/2010 | Perez et al. | |
| 7,695,926 B2 | 4/2010 | Perez et al. | |
| 7,734,557 B2 | 6/2010 | Meehan et al. | |
| 7,939,278 B2 | 5/2011 | Perez et al. | |
| 8,148,094 B2 | 4/2012 | Perez et al. | |
| 8,198,037 B2 | 6/2012 | Perez et al. | |
| 8,206,939 B2 | 6/2012 | Perez et al. | |
| 8,309,306 B2 | 11/2012 | Nolan et al. | |
| 8,778,620 B2 | 7/2014 | Fantl et al. | |
| 2002/0029235 A1 | 3/2002 | Lock et al. | |
| 2002/0079008 A1 | 6/2002 | Chien et al. | |
| 2002/0125139 A1 | 9/2002 | Chow et al. | |
| 2003/0078703 A1 | 4/2003 | Potts et al. | |
| 2004/0143423 A1 | 7/2004 | Parks et al. | |
| 2004/0220897 A1 | 11/2004 | Bernhart et al. | |
| 2004/0259111 A1 * | 12/2004 | Marlowe et al. | 435/6 |
| 2005/0009078 A1 | 1/2005 | Craford et al. | |
| 2005/0220671 A1 | 10/2005 | Stein et al. | |
| 2006/0015291 A1 | 1/2006 | Parks et al. | |
| 2006/0046272 A1 | 3/2006 | Chow et al. | |
| 2006/0134599 A1 | 6/2006 | Toner et al. | |
| 2006/0141549 A1 | 6/2006 | Mahajan et al. | |
| 2006/0210435 A1 | 9/2006 | Alavie et al. | |
| 2006/0258019 A1 | 11/2006 | Chow et al. | |
| 2007/0009923 A1 | 1/2007 | Nolan et al. | |
| 2007/0078626 A1 | 4/2007 | Orfao De Matos Correia E Vale et al. | |
| 2007/0118297 A1 | 5/2007 | Thayer | |
| 2007/0157973 A1 | 7/2007 | Chien et al. | |
| 2007/0196869 A1 | 8/2007 | Perez et al. | |
| 2007/0299799 A1 | 12/2007 | Meehan et al. | |
| 2008/0241820 A1 | 10/2008 | Krutzik et al. | |
| 2008/0254489 A1 | 10/2008 | Perez et al. | |
| 2009/0068681 A1 | 3/2009 | Perez et al. | |
| 2009/0081699 A1 | 3/2009 | Perez et al. | |
| 2009/0098594 A1 | 4/2009 | Fantl et al. | |
| 2009/0204557 A1 | 8/2009 | Zhang | |
| 2009/0269773 A1 | 10/2009 | Fantl et al. | |
| 2009/0269800 A1 | 10/2009 | Covey et al. | |
| 2009/0287421 A1 | 11/2009 | Malachowski et al. | |
| 2009/0291458 A1 | 11/2009 | Cohen et al. | |
| 2009/0307248 A1 | 12/2009 | Moser et al. | |
| 2009/0327240 A1 | 12/2009 | Meehan et al. | |
| 2010/0009364 A1 | 1/2010 | Fantl et al. | |
| 2010/0014741 A1 | 1/2010 | Banville et al. | |
| 2010/0030719 A1 | 2/2010 | Covey et al. | |
| 2010/0042351 A1 | 2/2010 | Covey et al. | |
| 2010/0070459 A1 | 3/2010 | Zigon et al. | |
| 2010/0070502 A1 | 3/2010 | Zigon | |
| 2010/0070904 A1 | 3/2010 | Zigon et al. | |
| 2010/0086951 A1 | 4/2010 | Hedley et al. | |
| 2010/0099109 A1 | 4/2010 | Fantl et al. | |
| 2010/0151472 A1 | 6/2010 | Nolan et al. | |
| 2010/0161561 A1 | 6/2010 | Moore et al. | |
| 2010/0184092 A1 | 7/2010 | Perez et al. | |
| 2010/0197512 A1 * | 8/2010 | Trinkle et al. | 506/7 |
| 2010/0204973 A1 | 8/2010 | Parkinson et al. | |
| 2010/0209929 A1 | 8/2010 | Fantl et al. | |
| 2010/0215644 A1 | 8/2010 | Fantl et al. | |
| 2010/0221750 A1 | 9/2010 | Perez et al. | |
| 2010/0228491 A1 | 9/2010 | Gutierrez et al. | |
| 2010/0233733 A1 | 9/2010 | Fantl | |
| 2010/0240542 A1 | 9/2010 | Soper et al. | |
| 2010/0285594 A1 | 11/2010 | Purvis, Jr. | |
| 2010/0297676 A1 | 11/2010 | Fantl et al. | |
| 2011/0059861 A1 | 3/2011 | Nolan et al. | |
| 2011/0104717 A1 | 5/2011 | Fantl et al. | |
| 2011/0201018 A1 | 8/2011 | Perez et al. | |
| 2011/0207145 A1 | 8/2011 | Perez et al. | |
| 2011/0207146 A1 | 8/2011 | Perez et al. | |
| 2011/0250614 A1 | 10/2011 | Perez et al. | |
| 2011/0262468 A1 | 10/2011 | Fantl et al. | |
| 2011/0269154 A1 | 11/2011 | Fantl et al. | |
| 2011/0269634 A1 | 11/2011 | Perez et al. | |
| 2012/0070849 A1 | 3/2012 | Perez et al. | |
| 2012/0157340 A1 | 6/2012 | Cesano et al. | |
| 2012/0215487 A1 | 8/2012 | Banville et al. | |
| 2013/0024177 A1 | 1/2013 | Nolan | |
| 2013/0034862 A1 | 2/2013 | Fantl et al. | |
| 2013/0035253 A1 | 2/2013 | Rosen et al. | |
| 2013/0071860 A1 | 3/2013 | Hale et al. | |
| 2013/0078621 A1 | 3/2013 | Nolan et al. | |
| 2013/0096948 A1 | 4/2013 | Parkinson et al. | |
| 2013/0122524 A1 | 5/2013 | Fantl et al. | |
| 2013/0123131 A1 | 5/2013 | Purvis et al. | |
| 2013/0129681 A1 | 5/2013 | Covey et al. | |
| 2014/0011222 A1 | 1/2014 | Fantl | |
| 2014/0017678 A1 | 1/2014 | Cesano et al. | |
| 2014/0031308 A1 | 1/2014 | Longo | |
| 2014/0040265 A1 | 2/2014 | Moser et al. | |
| 2014/0057865 A1 | 2/2014 | Fantl et al. | |
| 2014/0065633 A1 | 3/2014 | Fantl et al. | |
| 2014/0093903 A1 | 4/2014 | Ptacek et al. | |
| 2014/0120122 A1 | 5/2014 | Fantl et al. | |
| 2014/0127716 A1 | 5/2014 | Longo | |
| 2014/0134648 A1 | 5/2014 | Fantl et al. | |
| 2014/0134650 A1 | 5/2014 | Hawtin et al. | |
| 2014/0147857 A1 | 5/2014 | Fantl et al. | |
| 2014/0170698 A1 | 6/2014 | Purvis, Jr. | |
| 2014/0199273 A1 | 7/2014 | Cesano et al. | |
| 2015/0017119 A1 | 1/2015 | Fantl et al. | |

FOREIGN PATENT DOCUMENTS

| | | |
|---|---|---|
| WO | WO 03/067210 A2 | 8/2003 |
| WO | WO 03/067210 A3 | 12/2003 |
| WO | WO 2006/012507 A2 | 2/2006 |
| WO | WO 2006/079092 A2 | 7/2006 |
| WO | WO 2006/012507 A3 | 10/2006 |
| WO | WO 2007/117423 A2 | 10/2007 |
| WO | WO 2007/117423 A3 | 4/2008 |
| WO | WO 2008/088857 A2 | 7/2008 |

(56) References Cited

FOREIGN PATENT DOCUMENTS

| | | |
|---|---|---|
| WO | WO 2009/025847 A2 | 2/2009 |
| WO | WO 2009/025847 A3 | 6/2009 |
| WO | WO 2010/006291 A1 | 1/2010 |
| WO | WO 2010/006303 A2 | 1/2010 |
| WO | WO 2010/028277 A1 | 3/2010 |
| WO | WO 2010/045651 A1 | 4/2010 |
| WO | WO 2010/135608 A1 | 11/2010 |
| WO | WO 2011/031803 A1 | 3/2011 |
| WO | WO 2011/106558 A1 | 9/2011 |
| WO | WO 2011/119868 A2 | 9/2011 |
| WO | WO 2011/156654 A2 | 12/2011 |
| WO | WO 2012/024546 A2 | 2/2012 |
| WO | WO 2012/033537 A1 | 3/2012 |
| WO | WO 2012/083274 A2 | 6/2012 |
| WO | WO 2013/112948 A1 | 8/2013 |
| WO | WO 2013/188469 A2 | 12/2013 |
| WO | WO 2014/074646 A2 | 5/2014 |
| WO | WO 2014/081987 A1 | 5/2014 |
| WO | WO 2014/134570 A1 | 9/2014 |

OTHER PUBLICATIONS

Kumar, et al. 2-methoxyestradiol blocks cell-cycle progression at G(2)/M phase and inhibits growth of human prostate cancer cells. Mol Carcinog. Jul. 2001;31(3):111-24.

Mack, et al. Detection of caspase-activation in intact lymphoid cells using standard caspase substrates and inhibitors. J Immunol Methods. Jul. 31, 2000;241(1-2):19-31.

Benekli, et al. Signal transducer and activator of transcription proteins in leukemias. Blood. Apr. 15, 2003;101(8):2940-54.

Birkenkamp, et al. Regulation of constitutive STAT5 phosphorylation in acute myeloid leukemia blasts. Leukemia. 2001; 15(12):1923-31.

Chow, et al. Constitutive phosphorylation of the S6 ribosomal protein via mTOR and ERK signaling in the peripheral blasts of acute leukemia patients. Experimental hematology. 2006; 34(9):1182-1190.

Aguilera et al., Permeabilizing action of an antimicrobial lactoferricin-derived peptide on bacterial and artificial membranes. FEBS Lett. 1999. 462: 273-277.

Bussing et al., Expression of Mitichondrial Apo2.7 Molecules and Caspase-3 Activation in Human Lymphocytes Treated with the Ribosome-Inhibiting Mistletoe Lectins and the Cell Membrane Permeabilizing Viscotoxins. Cytometry. 1999. 37: 133-139.

Cheng X, Irimia, et. al., Practical label-free CD4+ T cell counting of HIV-infected subjects: A Microchip approach. Lab on a Chip 2007; 10:1039.

Francis et al. Rapid single-step method for flow cytometric detection of surface and intracellular antigens using whole blood, Cytometry. Sep. 1, 1996;25(1):58-70.

Goncalves et al., The use of permeabilized cells to assay protein phosphorylation and catecholamine release. Neurochem Res. 2000. 25(6):885-94.

Hanahan, et al. The Hallmarks of Cancer. Cell. 2000. 100(1):57-70.

Irimia D, Geba D, Toner M., Universal microfluidic gradient generator, Analytical Chemistry 2006; 78: 3472-3477.

Irish, et al. Mapping normal and cancer cell signalling networks: towards single-cell proteomics. Nat. Rev. Cancer. 2006. 6:146-155.

Irish, et al. Flt3 Y591 duplication and Bcl-2 overexpression are detected in acute myeloid leukemia cells with high levels of phosphorylated wild-type p53. Blood. 2007. 109(6):2589-96.

Irish, et al. Single cell profiling of potentiated phospho-protein networks in cancer cells. Cell. 2004. 118(2):217-28.

Krutzik, et al. High-content single-cell drug screening with phosphospecific flow cytometry. Natural Chemical Biology. 2008. 4(2):132-42.

Krutzik, et al. Intracellular phospho-protein staining techniques for flow cytometry: monitoring single cell signaling events. Cytometry A. 2003; 55(2): 61-70.

Krutzik. Characterization of the murine immunological signaling network with phosphospecific flow cytometry. J Immunol. 2005. 175(4): 2366-73.

Krutzik, et al. Coordinate analysis of murine immune cell surface markers and intracellular phosphoproteins by flow cytometry. J Immunol. 2005. 175(4):2357-65.

Krutzik et al. Fluorescent cell barcoding in flow cytometry allows high-throughput drug screening and signaling profiling. Nat Methods. May 2006;3(5):361-8.

Metso, T, et al., Identification of intracellular markers in induced sputum and bronchoalveolar lavage samples in patients with respiratory disorders and healthy persons. Respir Med. 2002. 96(11):918-26.

Shulz, et al. Single-Cell Phospho-Protein Analysis by Flow Cytometry. Current Protocols in Immunology. 2007;78:8.17.1-20.

Seiler, K. et al., "Electroosmotic Pumping and Valveless Control of Fluid Flow Within a Manifold of Capillaries on a Glass Chip," Anal. Chem. 66:3485-3491 (1994).

Stelzer et al. Use of Multiparameter Flow Cytometry and Immunophenotyping for the Diagnosis and Classification of Acute Myeloid Leukemia, Immunophenotyping, Wiley, 2000.

Van Hest et al., Efficient introduction of Alkene functionality into proteins in vivo. FEBS Letters. 1998. 428:(1-2) 68-70.

U.S. Appl. No. 13/384,181, filed Jan. 13, 2012, Cesano et al.

Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

Crans-Vargas, et al. CREB as a prognostic marker in acute leukemia. Abstract. Blood. 2001; 98(11), part 1, p. 316a.

European search report and search opinion dated Feb. 22, 2011 for Application No. 10180167.8.

Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.

Kornblau, et al. Dynamic single-cell network profiles in acute myelogenous leukemia are associated with patient response to standard induction therapy. Clin Cancer Res. Jul. 15, 2010;16(14):3721-33. (abstract).

Krutzik, et al. Analysis of protein phosphorylation and cellular signaling events by flow cytometry: techniques and clinical applications. Clinical Immunology. 2004; 110: 206-21.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Perez, et al. LFA-1 signaling through p44/42 is coupled to perforin degranulation in CD56+CD8+natural killer cells. Blood. Aug. 15, 2004;104(4):1083-93.

Perez, et al. Simultaneous measurement of multiple active kinase states using polychromatic flow cytometry. Nat Biotechnol. 2002; 20: 155-62.

Rosen, et al. Functional characterization of FLT3 receptor signaling deregulation in acute myeloid leukemia by single cell network profiling (SCNP). PLoS One. Oct. 27, 2010;5(10):e13543.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005;7(4):351-62.

Spiekermann, et al. Overexpression and constitutive activation of FLT3 induces STAT5 activation in primary acute myeloid leukemia blast cells. Clinical Cancer Research. Jun. 2003; 9:2140-2150.

UK office action and search report dated Feb. 22, 2011 for GB Application No. 1017857.2.

Zheng, et al. Regulation of STAT3 and STAT5 in the differentiation of FLT3/ITD expressing 32Dcl3 cells induced by G-CSF and CEP-701. Abstract 2935.Blood. 2002; 100(11) and 44th Annual Meeting of the American Society of Hematology. Philadelphia, PA, USA. Dec. 6-10, 2002.

(56) References Cited

OTHER PUBLICATIONS

About Cytobank—Cytobank documentation. Accessed: Oct. 1, 2012 http://docs.cytobank.org/wagn/About_Cytobank, 1 pg.
About Cytobank, Cytobank. Accessed: Oct. 1, 2012. http://www.cytobank.org/about/about.html, 1 pg.
Demirci, et al. Direct etch method for microfludic channel and nanoheight post-fabrication by picoliter droplets. Applied Physics Letters. Jan 2006; 88(5):053117-053117-3.
Examination Report dated Jan. 31, 2012 for Application No. GB1 102311.6.
Fluorophore selection guide for flow cytometry invitrogen guide © 2007; 44 pages.
Gait. Oligonucleotide synthesis: a practical approach. Table of Contents, 1989; 7 pgs.
Huyn. Scientific OLAP for the Biotech Domain, Proceedings of the 27th VLDB Conference, Roma, Italy, 2001.
International Search Report and Written Opinion dated Mar. 4, 2010 for PCT/US2009/50307.
Koontz, et at. A Nonparametric Valley-Seeking Technique for Cluster Analysis. Feb. 1972, IEEE Transactions on Computers, vol. C-21, No. 2, pp. 171-178.
Lugli, et al. Subject classification obtained by cluster analysis and principal component analysis applied to flow cytometric data. Cytometry A. May 2007;71(5):334-44.
Mansmann, et al. Hierarchy-driven Visual Exploration of Multidimensional data Cubes. Konstanzer Online-Publikations-System (KOPS). 2007. [online] retrieved from the Internet http://www.ub.uni-konstanz.de/kops/volltexte/2008/6878/.
Multicolor Flow Cytometry Demystified, Copyright 2007 Invitrogen Corporation, http://www.invitrogen.com/etc/medialib/en/filelibrary/pdf/bioprobes.Par.0366.File.dat/BP53_03.pdf, 1 pg. Accessed: Oct. 1, 2012.
Office action dated Oct. 20, 2011 for U.S. Appl. No. 12/501,295.
Office action dated Oct. 24, 2011 for U.S. Appl. No. 12/501,274.
Saez-Rodriguez, et al. Flexible informatics for linking experimental data to mathematical models via DataRail. Bioinformatics. Mar. 15, 2008;24(6):840-7. Epub Jan. 24, 2008.
Seller, et al., "Electroosmotic Pumping and Valveless Control of Fluid Flow within a Manifold of Capillaries on a Glass Chip," Anal. Chem. 1994, vol. 66, No. 20, Oct. 15, 1994, pp. 3485-3491.
Stewart, et al., "Immunophenotyping,"© 2000 by Wiley-Liss, Inc.
TruCulture® Blood Collection and Whole Blood Culture System (RUO), TruCulture—GW I Myriad RBM, pp. 3. 2011. Accessed: Oct. 1, 2012. http://www.rulesbasedmedicine.com/products-services/truculture/GW.
UK search and examination report dated Jul. 31, 2012 for GB Application No. 1102311.6.
Visvalingam, et al. The Douglas-Peucker Algorithm for Line Simplification: Re-evaluation through Visualization. Sep. 1990 Computer Graphics Forum. 213-225.
Whyatt, et al. The Douglas-Peucker Line Simplification Algorithm. 1988 Society of University Cartographers, Bulletin 22(1): 17-25.
U.S. Appl. No. 13/750,700, filed Jan. 25, 2013, Longo.
U.S. Appl. No. 13/801,420, filed Mar. 13, 2013, Cesano et al.
U.S. Appl. No. 13/821,539, filed Mar. 7, 2013, Longo.
U.S. Appl. No. 13/900,170, filed May 22, 2013, Fantl.
PCT/US2013/045273, filed Jun. 11, 2013, Cesano et al.
U.S. Appl. No. 13/913,029, filed Jun. 7, 2013, Fantl et al.
U.S. Appl. No. 13/958,285, filed Aug. 2, 2013, Fantl et al.
U.S. Appl. No. 14/011,715, filed Aug. 27, 2013, Ptacek et al.
U.S. Appl. No. 14/013,567, filed Aug. 29, 2013, Purvis Jr.
U.S. Appl. No. 14/014,110, filed Aug. 29, 2013, Moser et al.
U.S. Appl. No. 14/036,216, filed Sep. 25, 2013, Fantl et al.
PCT/US2013/068815, filed Nov. 6, 2013, Hawtin et al.
PCT/US2013/071354, filed Nov. 21, 2013, Cesano et al.
U.S. Appl. No. 14/045,548, filed Oct. 3, 2013, Fantl et al.
U.S. Appl. No. 14/072,623, filed Nov. 5, 2013, Longo.
U.S. Appl. No. 14/073,692, filed Nov. 6, 2013, Hawtin et al.
U.S. Appl. No. 14/086,922, filed Nov. 21, 2013, Cesano et al.
Jacobberger. Flow Cytometric Analysis of Intracellular Protein Epitopes. Immunophenotyping. 2000; 361-409.
U.S. Appl. No. 14/193,746, filed Feb. 28, 2014, Ptacek et al.
U.S. Appl. No. 14/279,905, filed May 16, 2014, Fantl et al.
U.S. Appl. No. 14/294,592, filed Jun. 3, 2014, Fantl et al.
U.S. Appl. No. 14/450,639, filed Aug. 4, 2014, Soper et al.
U.S. Appl. No. 13/094,735, filed Apr. 26, 2011, Perez et al.
U.S. Appl. No. 13/094,737, filed Apr. 26, 2011, Perez et al.
U.S. Appl. No. 13/453,636, filed Apr. 23, 2012, Purvis Jr.
U.S. Appl. No. 13/464,254, filed May 4, 2012, Moser et al.
U.S. Appl. No. 13/473,829, filed May 17, 2012, Fantl et al.
U.S. Appl. No. 13/493,857, filed Jun. 11, 2012, Fantl et al.
U.S. Appl. No. 13/544,053, filed Jul. 9, 2012, Soper et al.
U.S. Appl. No. 14/572,317, filed Dec. 16, 2014, Fantl et al.
U.S. Appl. No. 14/574,277, filed Dec. 17, 2014, Fantl et al.

\* cited by examiner

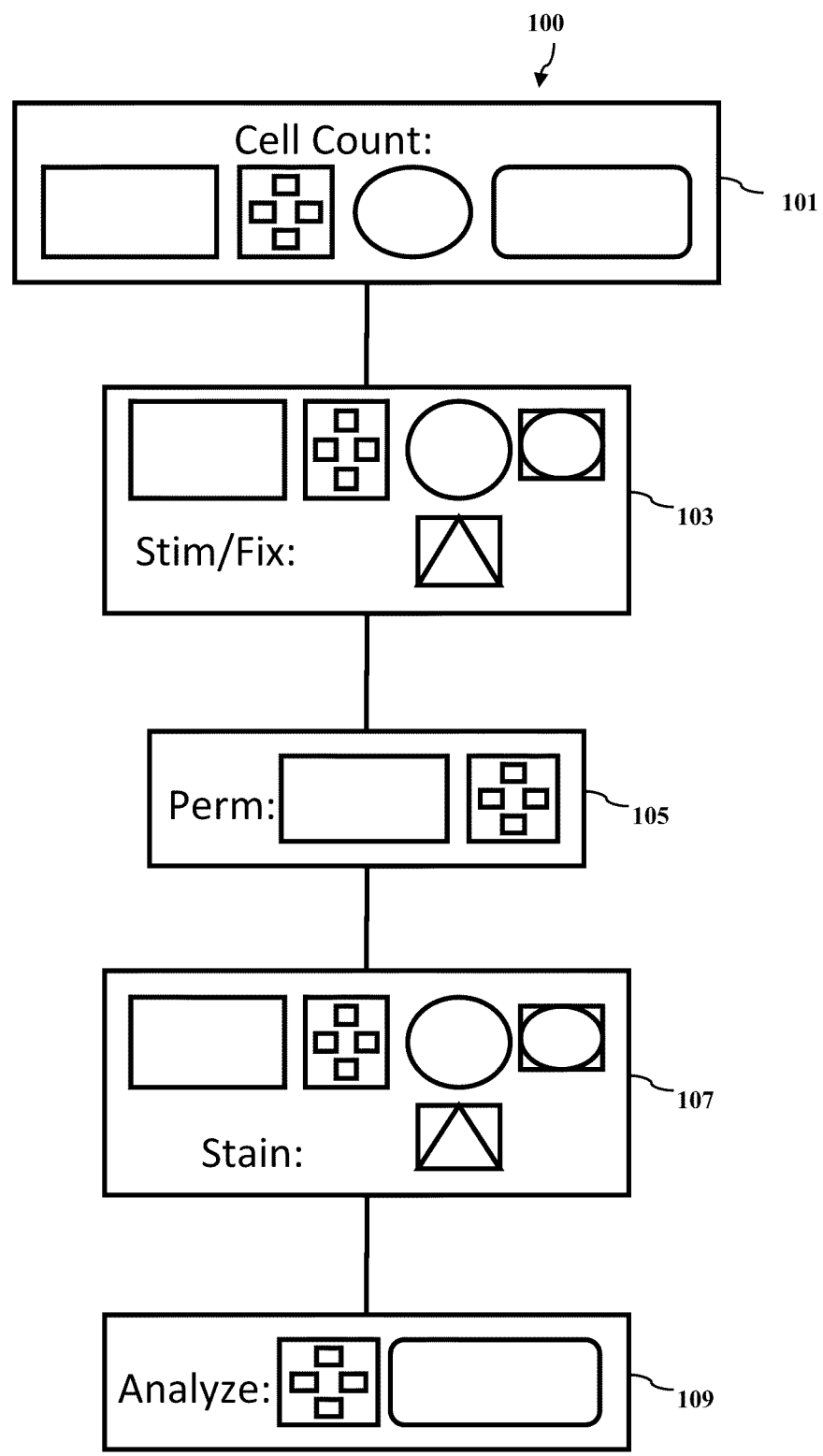

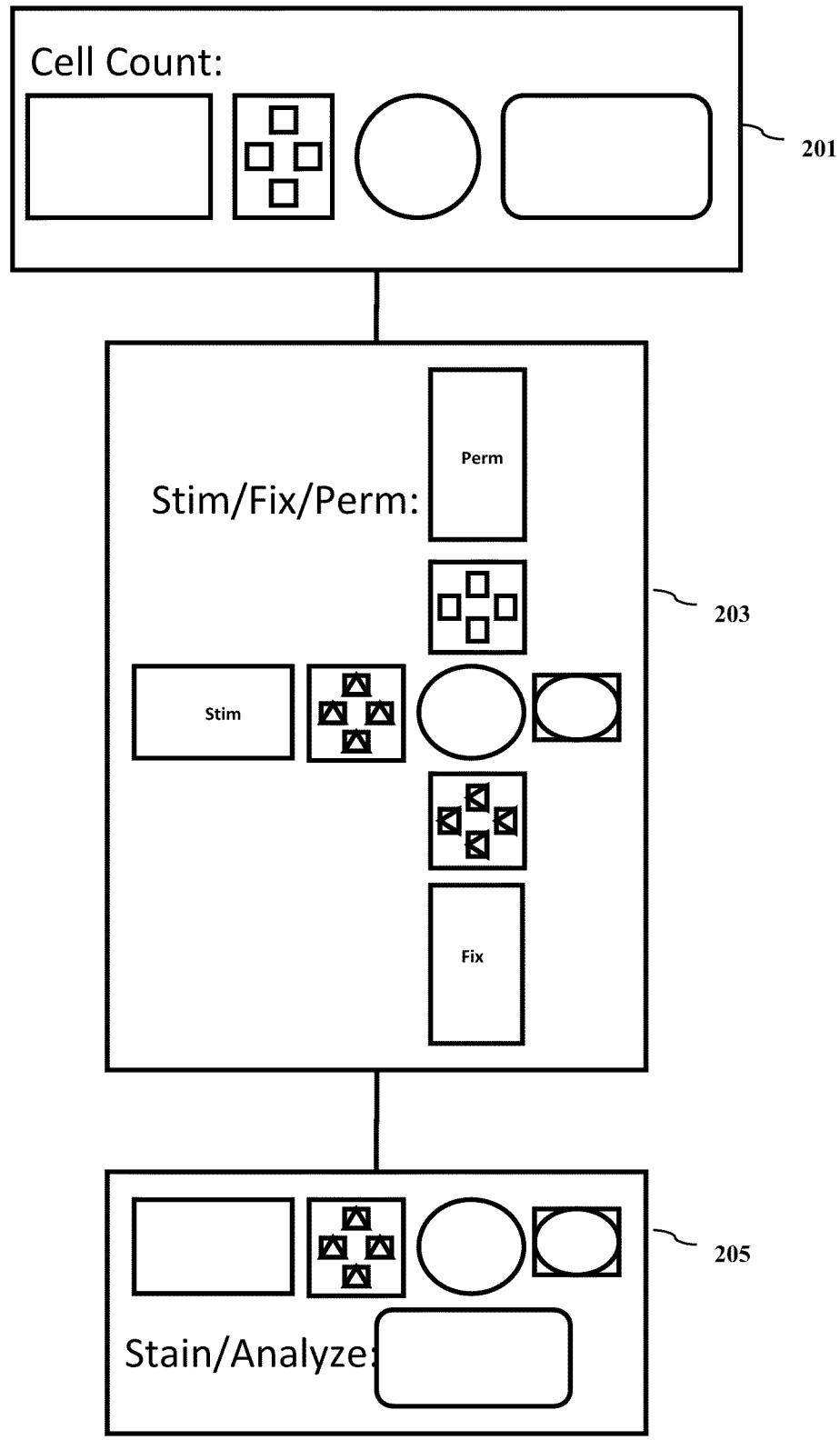

US 9,034,257 B2

HIGH THROUGHPUT FLOW CYTOMETRY SYSTEM AND METHOD

CROSS-REFERENCE

This application claims the benefit of U.S. Provisional Applications Nos. 61/108,803 filed Oct. 27, 2008, 61/162,598 filed Mar. 23, 2009, and 61/181,211 filed May 26, 2009, which application is incorporated herein by reference.

BACKGROUND OF THE INVENTION

Cell preparation for analysis using a flow cytometer is commonly used for monitoring progression of disease, monitoring therapy, and for screening compounds that may be used to treat a disease.

Current techniques offer little in the way of automation for preparing samples and analyzing them using flow cytometry. Current protocols for cell preparation are mostly performed by human operators. This means that sample throughput is limited to what a single person or team of people can accomplish in a given amount of time.

Accordingly, there is a need for a process that has the advantage of generating less labor intensive and more reproducible results. It is advantageous to generate reliable data from highly controlled complex laboratory automation for the study of cell signaling and for drug screening either in the form of complete walk-away automation or with user intervention at defined points. A highly controlled automated process can increase throughput, reduce the potential for introducing variability into the results, and ensure that meaningful results are generated.

SUMMARY OF THE INVENTION

The present invention relates to the processing of cells for analysis. More specifically, the present invention relates to a high throughput process and system for analyzing cells using a flow cytometer.

In accordance with one embodiment described herein, a system is described that facilitates automated and high-throughput processing of cell samples for flow cytometry. In some embodiments, the invention describes a system that facilitates automated and high-throughput processing of cell samples for phosphoflow cytometry. In some embodiments, the invention describes a system that facilitates automated and high-throughput processing of cell samples for analyzing receptor function (e.g. drug transporter) using flow cytometry. This system includes one or more robotic liquid handling instruments capable of performing sample transfer, reagent addition, mixing, aspiration, incubation, and centrifugation on a plurality of microplates or cartridges containing biological materials. One embodiment is comprised of multiple automation systems that perform fewer functions and may require some human intervention. One embodiment is a fully automated system.

Particular embodiments are integrated systems for performing flow cytometry assays, acquisition, compilation, storage, and analysis of data. These systems may include one or more robotic liquid handling instruments with or without barcode scanners, operably linked to one or more digital computers with software including an instruction set, an input device, and a user interface to input plate data.

In a particular embodiment, automated and semi-automated instruments, as well as peripheral equipment, exchange sample information and other relevant processing data with a laboratory integrated management system (LIMS). In a particular embodiment, applications and instruments may communicate with, or receive information from LIMS.

In a particular embodiment, the cytometer is part of the automated platform which may contain a liquid handler, automated centrifuge (V-spin), incubator, Hypercyte, cytometer controlled by a scheduling software, and a pathway analysis tool at the back end. In a particular embodiment, the system be an automated approach to pathway profiling starting from sample (i.e., blood, marrow, purified cells, cell lines) and ending with a full signaling pathway work-up. In a particular embodiment, the system may be an automated or semi-automated instrument that may be operably linked to a computational device equipped with user input and output features.

In accordance with a particular embodiment, a method is described for automatic retrieval of a plurality of microplates, as well as automatic sample transfer, reagent addition, mixing, aspiration, incubation, and centrifugation of those microplates. The method may include the steps of retrieving a selected microplate from the plate holder, performing specified steps of the assay on that plate in a controlled and timed fashion, and then the final step of returning the completed microplate to the plate holder.

Applications of the present invention may include probing the various pathways by analyzing responses to a host of stimuli. Applications may also include using the system in combination with a compound library to assess the inhibition or enhancement of various signaling nodes, assessing expression level and functionality of various drug transporters, or probing the signaling differences among various cancer cell lines (i.e., NCI 60 cell lines). Examples of drug transporters include, but are not limited to, glycoprotein (MDR1), MDR—associated protein and breast cancer resistance protein. Particular embodiments may be used to screen the supernatants from hybridomas in order to pick the best antibody secreting cell clone. For instance, one could screen for a neutralizing or agonistic antibody to a growth factor receptor by looking for the supernatant that best augments the signaling downstream of the growth factor receptor. In another embodiment one could use the platform to select the best cell clone secreting any protein that has a biological effect that could be measured by its downstream effect on signaling.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates a partially automated system that facilitates high-throughput processing of cell samples for phosphoflow cytometry.

FIG. 2 illustrates a partially automated system that facilitates high-throughput processing of cell samples for phosphoflow cytometry.

DETAILED DESCRIPTION OF THE INVENTION

Figure 3A:
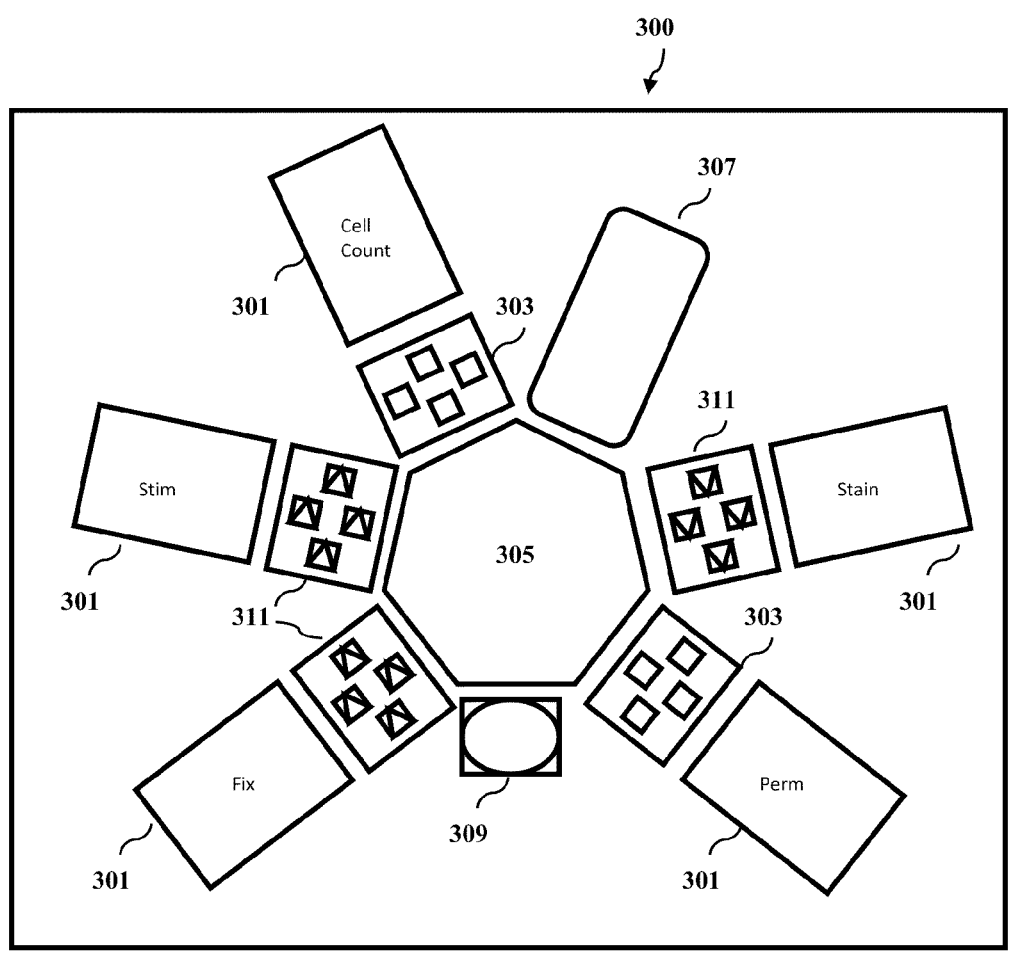
FIG. 3A illustrates a fully automated system that facilitates high-throughput processing of cell samples for phosphoflow cytometry.

High throughput flow cytometry system and method has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Particular embodiments of the high throughput flow cytometry system are designed to automate and improve the throughput of flow cytometry systems, especially those that analyze cell signaling networks and cell receptor function. Particular embodiments of the automated system provide a highly controlled platform to screen large numbers of samples that may then be analyzed using multiparametric flow cytometry. Particular embodiments of the automated system may be used in research and development, diagnostic testing, clinical trials, testing cell lines, drug screening and drug discovery applications. Particular embodiments of the automated system may be designed to reduce processing cost, reduce processing variability, or improve data integrity.

Particular embodiments comprise fully integrated, highly controlled automated sample processing. In a particular embodiment, a robotic arm may operate around a variety of instruments that are involved in sample preparation for the analysis. Those instruments may include a flow cytometer, a sample acquisition device (Hypercyt for example), microcentrifuge tubes holding cell samples, microplates holding cell samples, centrifuges, reagent containers, temperature controlled incubators, thermal cyclers, temperature controlled refrigeration units, liquid handling devices, automated pipetting devices, automated dispensers, plate sealers, plate piercers, barcode scanners, plate holders and may be operated by a computer running the appropriate software using the appropriate graphical user interface (GUI), which may be integrated into a laboratory information management system (LIMS). In a particular embodiment, the robotic arm may remove microplates containing cell samples from an incubator or plate holder, the plates would be placed on a deck as a working surface to interact with other instruments and to accept the appropriate reagents. A liquid handling or micropetting assembly may pull reagents from a plate and add them to the cells (or vice versa). Scheduling software may measure the appropriate incubation times and stop the reaction when necessary. The cycles may be repeated as required for the stimulation and preparation of the cells for flow cytometer analysis and the cells may be centrifuged and washed to prepare a pellet. The robotic arm may take the cell sample and pass to a refrigeration unit for preservation or may subject it to immediate analysis.

Particular embodiments comprise islands of automation requiring human intervention to move samples from one process to the next. In a particular embodiment a plurality of components are involved with sample preparation for sample analysis. Those components may include a flow cytometer, a sample acquisition device (Hypercyt for example), microcentrifuge tubes holding cell samples, microplates holding cell samples, centrifuges, reagent containers, temperature controlled incubators, thermal cyclers, temperature controlled refrigeration units, liquid handling devices, automated pipetting devices, automated dispensers, plate sealers, plate piercers, barcode scanners, plate holders and each instrument may be operated by computers running the appropriate software using the appropriate graphical user interface (GUI), which may be integrated into a laboratory information management system (LIMS).

Background Information

Particular embodiments of the high throughput flow cytometry system and method incorporate information disclosed in other applications and texts. The following patents and other publications are hereby incorporated by reference in their entireties: Haskell et al, Cancer Treatment, 5th Ed., W.B. Saunders and Co., 2001; Alberts et al., The Cell, 4th Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7th Ed., Garland, and Leroith and Bondy, Growth Factors and Cytokines in Health and Disease, A Multi Volume Treatise, Volumes 1A and 1B, Growth Factors, 1996. Patents and applications that are also incorporated by reference include U.S. Pat. No. 7,314,595, U.S. Pat. No. 7,368,084, U.S. Pat. No. 7,381,535 and U.S. Pat. No. 7,393,656 and U.S. patent application Ser. Nos. 10/193,462; 11/655,785; 11/655,789; 11/655,821; 11/338,957, 61/048,886; 61/048,920; 61/048,657; 61/055,362; 61/079,766; 61/085,789; 61/079,551; 61/079,537; 61/079,579; 61/087,555; 61/120,320; and 61/153,627. Relevant articles include High-content single-cell drug screening with phosphospecific flow cytometry, Krutzik et al., Nature Chemical Biology, 23 Dec. 2007; Irish et al., FLt3 ligand Y591 duplication and Bcl-2 over expression are detected in acute myeloid leukemia cells with high levels of phosphorylated wild-type p53, Neoplasia, 2007, Irish et al. Mapping normal and cancer cell signaling networks: towards single-cell proteomics, Nature, Vol. 6 146-155, 2006; and Irish et al., Single cell profiling of potentiated phospho-protein networks in cancer cells, Cell, Vol. 118, 1-20 Jul. 23, 2004; Schulz, K. R., et al., Single-cell phospho-protein analysis by flow cytometry, Curr Protoc Immunol, 2007, 78:8 8.17.1-20; Krutzik, P. O., et al., Coordinate analysis of murine immune cell surface markers and intracellular phosphoproteins by flow cytometry, J Immunol. 2005 Aug. 15; 175(4):2357-65; Krutzik, P. O., et al., Characterization of the murine immunological signaling network with phosphospecific flow cytometry, J Immunol. 2005 Aug. 15; 175(4): 2366-73; Shulz et al., Current Protocols in Immunology 2007, 78:8.17.1-20; Stelzer et al. Use of Multiparameter Flow Cytometry and Immunophenotyping for the Diagnosis and Classification of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. 2003 October; 55(2):61-70; Hanahan D., Weinberg, The Hallmarks of Cancer, CELL, 2000 Jan. 7; 100(1) 57-70; Krutzik et al, High content single cell drug screening with phosphospecific flow cytometry, Nat Chem Biol. 2008 February; 4(2):132-42. Experimental and process protocols and other helpful information can be found at http:/proteomices.stanford.edu. Articles and other references that may be cited below are also incorporated by reference in their entireties for all purposes. Some commercial reagents, protocols, software and instruments that are useful in particular embodiments of the present invention are available at the Becton Dickinson Website http:(slashslash)www.bdbiosciences.com/features/products/, and the Beckman Coulter website, http:(slashslash)www.beckmancoulter.com/Default.asp?bhfv=7.

In addition to the references cited above, the practice of the present invention may employ, unless otherwise indicated, conventional techniques and descriptions of flow cytometry, organic chemistry, polymer technology, molecular biology (including recombinant techniques), cell biology, cancer biology, biochemistry, and immunology, which are within the skill of the art. Such conventional techniques can be found in articles, patents, commercial websites, as well as other sources as referenced above. Other conventional techniques can be shown in standard laboratory manuals such as those recited above and also including Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry ($4^{th}$ Ed.) Freeman, N.Y., Gait, "Oligonucleotide Synthesis: A Practical Approach" 1984, IRL Press, London, Nelson and Cox (2000), Lehninger, Principles of Biochemistry $3^{rd}$ Ed., W.H. Freeman Pub., New York, N.Y. and Berg et al. (2002) Biochemistry, $5^{th}$ Ed., W.H. Freeman Pub., New York, N.Y., all of which are herein incorporated in their entirety by reference for all purposes.

Use of Computers

Particular embodiments of high throughput flow cytometry system may be implemented in a localized or distributed computing environment. For example, in a particular embodiment featuring a localized computing environment, a flow cytometry system may be operably linked to a computational device equipped with user input and output features. In a distributed environment, the methods may be implemented on a single computer, a computer with multiple processes or, alternatively, on multiple computers. The computers may be linked, e.g., through a shared bus, but more commonly, the computer(s) are nodes on a network. The network may be generalized or dedicated, at a local level or distributed over a wide geographic area. In particular embodiments, the computers may be components of an intranet or an internet. See U.S. Patent Application No. 61/048,657 and U.S. Pat. No. 7,314,595 which are incorporated by reference in its entirety for details of some computer hardware that may be useful in the present invention.

Particular embodiments also contemplate the use of a computer which may operate various instrumentation components, liquid handling or micropipetting equipment, analysis instruments or analysis software. The computer may be any type of computer platform such as a workstation, a personal computer, a server, or any other present or future computer. The computer typically includes known components such as a processor, an operating system, system memory, memory storage devices, and input-output controllers, input-output devices, and display devices. Display devices may include display devices that provides visual information, this information typically may be logically and/or physically organized as an array of pixels. A Graphical the user interface (GUI) controller may also be included that may comprise any of a variety of known or future software programs for providing graphical input and output interfaces such as for instance GUI's. For example, GUI's may provide one or more graphical representations to a the user, and also be enabled to process the user inputs via GUI's using means of selection or input known to those of ordinary skill in the related art.

It will be understood by those of ordinary skill in the relevant art that there are many possible configurations of the components of a computer and that some components that may typically be included in a computer are not shown, such as cache memory, a data backup unit, and many other devices. The processor may be a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Some embodiments of the processor may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that the processor may be configured in what is generally referred to as 32 or 64 bit architectures, or other architectural configurations now known or that may be developed in the future.

The processor executes an operating system, which may be, for example, a Windows®-type operating system (such as Windows® XP or Windows® Vista) from the Microsoft Corporation; the Mac OS X operating system from Apple Computer Corp. (such as 7.5 Mac OS X v10.4 "Tiger" or 7.6 Mac OS X v10.5 "Leopard" operating systems); a Unix® or Linux-type operating system available from many vendors or what is referred to as an open source; another or a future operating system; or some combination thereof. The operating system interfaces with firmware and hardware in a well-known manner, and facilitates processor in coordinating and executing the functions of various computer programs that may be written in a variety of programming languages. The operating system, typically in cooperation with the processor, coordinates and executes functions of the other components of computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, or other memory storage device. Memory storage devices may be any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software applications, also called computer control logic, typically are stored in system memory and/or the program storage device used in conjunction with memory storage device.

Input-output controllers could include any of a variety of known devices for accepting and processing information from a user, whether a human or a machine, whether local or remote. Such devices include, for example, modern cards, wireless cards, network interface cards, sound cards, or other types of controllers for any of a variety of known input devices. Output controllers of input-output controllers could include controllers for any of a variety of known display devices for presenting information to a user, whether a human or a machine, whether local or remote. In a particular embodiment, the functional elements of computer may communicate with each other via system bus. Some of these communications may be accomplished in alternative embodiments using network or other types of remote communications.

In a particular embodiment, the computer implemented methods and/or systems may be operated locally on a computer, on a network server accessed through one or more terminals, or through one or more machines accessed through an intranet or internet. The method may also be implemented through a computer readable medium storing a computer program implementing the method's functionality.

In particular embodiments, a computer application product may comprise a computer-readable medium having control logic (computer software program, including program code) stored therein. The control logic, when executed by a processor, causes the processor to perform functions described herein. In particular embodiments, some functions may be primarily implemented in hardware using a hardware state machine. Implementation of the hardware state machine so as to perform the functions described herein will be apparent to those skilled in the relevant arts.

As will be evident to those skilled in the relevant art, an instrument control and image processing application, such as for instance an implementation of instrument control and image processing applications, if implemented in software, may be loaded into and executed from system memory and/or memory storage device. All or portions of the instrument control and image processing applications may also reside in a read-only memory or similar device of memory storage device, such devices not requiring that the instrument control and image processing applications first be loaded through input-output controllers. It will be understood by those skilled in the relevant art that the instrument control and image processing applications, or portions of it, may be loaded by processor in a known manner into system memory, or cache memory (not shown), or both, as advantageous for execution. Library files, calibration data, experiment data, and internet client data may be stored in system memory. For example, experiment data could include data related to one or more experiments or assays such as excitation wavelength ranges, emission wavelength ranges, extinction coefficients and/or associated excitation power level values, or other values associated with one or more fluorescent labels. Additionally, internet client may include an application enabled to accesses a remote service on another computer using a network that may for instance comprise what are generally referred to as "Web Browsers". In the present example some commonly employed web browsers include Microsoft® Internet Explorer 7 with SPI available from Microsoft Corporation, Mozilla Firefox® 1.5 from the Mozilla Corporation, Safari 2.0 from Apple Computer Corp., or other type of web browser currently known in the art or to be developed in the future. In particular embodiments, the internet client may include, or could be an element of, specialized software applications enabled to access remote information via a network such as network.

The network may include one or more of the many various types of networks well known to those of ordinary skill in the art. For example, the network may include a local or wide area network that employs what is commonly referred to as a TCP/IP protocol suite to communicate, that may include a network comprising a worldwide system of interconnected computer networks that is commonly referred to as the internet, or could also include various intranet architectures. Those of ordinary skill in the related arts will also appreciate that some the users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by the users, such as for instance network administrators, etc.

Instrument control and image processing applications may comprise any of a variety of known or future image processing applications. Typically, particular embodiments of applications may be loaded into system memory and/or memory storage device.

In particular embodiments, applications may be stored on a server or computer that may be accessed located locally or remotely and communicate with one or more additional servers and/or one or more other computers/workstations or instruments. In a particular embodiment, applications may communicate with, and receive instruction or information from, or control one or more elements or processes of one or more servers, one or more workstations, and one or more instruments or system components.

In particular embodiments, automated and semi-automated instruments as well as peripheral equipment exchange sample information with a laboratory integrated management system (LIMS) or laboratory information system (LIS). In a particular embodiment, applications and components may communicate with, or receive information from LIMS or LIS. LIMS or LIS is typically associated with a computer workstation containing software applications, GUI, or instruments, and automates sample tracking from initial input into the system to data analysis. For example, see U.S. Patent Application No. 61/079,537.

Those skilled in the art will appreciate that applications may be stored for execution on any compatible computer system, such as computer, or any compatible computer readable tangible medium. Embodiments of applications may advantageously provide what is referred to as a modular interface for one or more computers or workstations and one or more servers, as well as one or more instruments. The term "modular" as used herein generally refers to elements that may be integrated to and interact with a core element in order to provide a flexible, updateable, and customizable platform. For example, as will be described in greater detail below applications may comprise a "core" software element enabled to communicate and perform primary functions necessary for any instrument control and image processing application. Such primary functionality may include communication over various network architectures, or data processing functions such as processing raw intensity data into a data file. In a particular embodiment, modular software elements, such as for instance what may be referred to as a plug-in module, may be interfaced with the core software element to perform more specific or secondary functions, such as for instance functions that are specific to particular instruments. In particular, the specific or secondary functions may include functions customizable for particular applications desired by the user. Further, integrated modules and the core software element are considered to be a single software application, and referred to as applications.

Web Site Embodiment

A website or alternatively what is known in the art as "cloud computing" embodiment may be used where typically; a user (e.g., a scientist) executes a Web browser and is linked to a server computer executing a Web server. In the present example some commonly employed web browsers include Microsoft® Internet Explorer 7 with SPI available from Microsoft Corporation, Mozilla Firefox® 1.5 from the Mozilla Corporation, Safari 2.0 from Apple Computer Corp., or other type of web browser currently known in the art or to be developed in the future. The Web server may be a program such as IBM's HTTP Daemon or other WWW daemon (e.g., LINUX-based forms of the program). The client computer may be bi-directionally coupled with the server computer over a line or via a wireless system. In turn, the server computer may be bi-directionally coupled with a website (server hosting the website) providing access to software implementing the methods of this invention.

In particular embodiments, a user of a client connected to the Intranet or Internet may cause the client to request resources that are part of the web site(s) hosting the application(s) providing an implementation of the methods or systems of this invention. Server program(s) or APIs running on the server then process the request to return the specified resources (assuming they are currently available), e.g. a browser running an application that displays the selected visualizations and metrics of an implementation described above. A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS").

In a particular embodiment, when a resource is downloaded, it may include the URLs of additional resources. Thus, the user of the client may easily learn of the existence of new resources that he or she had not specifically requested. One example of such an implementation would be a user on a remote machine using a web browser to make procedure calls, such as through an implementation of XML-RPC, discussed at http://www.xmlrpc.com, or Simple Object Access Protocol (SOAP), to a server application with an API for implementing the system or methods of the invention. The user through the web browser may be able to access all system functionality through a remote location with a server running the applications implementing the methods or systems of the invention.

Methods of implementing Intranet and/or Intranet embodiments of computational and/or data access processes are well known to those of skill in the art and are documented, e.g., in ACM Press, pp. 383-392; ISO-ANSI, Working Draft, "Information Technology-Database Language SQL", Jim Melton, Editor, International Organization for Standardization and American National Standards Institute, July. 1992; ISO Working Draft, "Database Language SQL-Part 2: Foundation (SQL/Foundation)", CD9075-2:199.chi.SQL, Sep. 11, 1997; and Cluer et al. (1992) A General Framework for the Optimization of Object-Oriented Queries, Proc SIGMOD International Conference on Management of Data, San Diego, Calif., Jun. 2-5, 1992, SIGMOD Record, vol. 21, Issue 2, June, 1992; Stonebraker, M., Editor. Other resources are available, e.g., from Microsoft, IBM, Sun and other software development companies.

Integrated Systems

Integrated systems, e.g., for performing flow cytometry assays and data analysis, as well as for the compilation, storage and access of databases, typically include a digital computer with software including an instruction set as described herein, and, optionally, one or more of high-throughput sample control software, image analysis software, other data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system may further comprise an image scanner for digitizing label signals from labeled assay components.

In particular embodiments, readily available computational hardware resources using standard operating systems may be employed and modified according to the teachings provided herein, e.g., a PC running for example, a Windows®-type operating system (such as Windows® XP or Windows® Vista) from the Microsoft Corporation; the Mac OS X operating system from Apple Computer Corp. (such as 7.5 Mac OS X v10.4 "Tiger" or 7.6 Mac OS X v10.5 "Leopard" operating systems); a Unix® or Linux-type operating system available from many vendors or what is referred to as an open source; another or a future operating system; or some combination thereof for use in the integrated systems of the invention. Current art in software technology is adequate to allow implementation of the methods taught herein on a computer system. Thus, in particular embodiments, the present invention may comprise a set of logic instructions (either software, or hardware encoded instructions) for performing one or more of the methods as taught herein. For example, software for providing the described data, visualization, and/or statistical analysis may be constructed by one of skill using a standard programming language such as Python, Visual Basic, Fortran, Basic, Java, C++, C#, or the like. Such software may also be constructed utilizing a variety of statistical programming languages, toolkits, or libraries.

In particular embodiments, various programming methods and algorithms, including genetic algorithms and neural networks, may be used to perform aspects of the data collection, correlation, and storage functions, as well as other desirable functions, as described herein. In addition, digital or analog systems such as digital or analog computer systems may control a variety of other functions such as the display and/or control of input and output files. Software for performing the visualization methods of the invention, such as programmed embodiments of the visualization methods described above, are also included in the computer systems of the invention. Alternatively, programming elements for performing such methods as principle component analysis (PCA) or least squares analysis may also be included in the digital system to identify relationships between data. Exemplary software for such methods is provided by Partek, Inc., St. Peter, Mo.; available at http://www.partek.com. Optionally, the integrated systems of the invention include an automated workstation.

In particular embodiments, automated and/or semi-automated methods for solid and liquid phase high-throughput sample preparation and evaluation are available, and supported by commercially available devices. For example, robotic devices for preparation of nucleic acids from bacterial colonies, e.g., to facilitate production and characterization of the libraries of candidate genes include, for example, an automated colony picker (e.g., the Q-bot, Genetix, U.K.) capable of identifying, sampling, and inoculating up to 10,000/4 hrs different clones into 96 well microtiter dishes. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Additionally, incubators, refrigerators, freezers, plate sealers, reagent dispensers, and barcode scanners may be necessary to augment the robotic systems at the appropriate processing steps. Any of the above devices are suitable for use with the present invention, e.g., for high-throughput analysis of library components or subject samples. The nature and implementation of modifications to these devices (if any) so that they may operate as discussed herein will be apparent to persons skilled in the relevant art.

A variety of commercially available peripheral equipment, including, e.g., flow cytometers and related optical and fluorescent detectors, and the like, and software are available for digitizing, storing and analyzing a digitized video or digitized optical or other assay results using a computer. Commercial Suppliers of flow cytometry instrumentation include Beckman Coulter, Inc. (Fullerton, Calif.), and Becton Dickinson (San Jose, Calif.), among many others.

In particular embodiments, applications may be capable of data encryption/decryption functionality. For example, it may be desirable to encrypt data, files, information associated with GUI's or other information that may be transferred over network to one or more remote computers or servers for data security and confidentiality purposes. In some applications, the one-way encrypted data may be stored in one or more public databases or repositories where even the curator of the database or repository would be unable to associate the data with the user or otherwise decrypt the information. The described encryption functionality may also have utility in clinical trial applications where it may be desirable to isolate one or more data elements from each other for the purpose of confidentiality and/or removal of experimental biases.

Particular embodiments provide one or more interactive graphical user interfaces that allow the user to make selections based upon information presented in an embodiment of GUI. Those of ordinary skill will recognize that embodiments of GUI may be coded in various language formats such as an HTML, XHTML, XML, javascript, Jscript, or other language known to those of ordinary skill in the art used for the creation or enhancement of "Web Pages" viewable and compatible with internet client, or other languages known or developed in the future for use in the creation of computer GUIs. For example, the internet client may include various internet browsers such as Microsoft Internet Explorer, Mozilla Firefox, Apple Safari, or other browsers known in the art. Applications of GUI's viewable via one or more browsers may allow the user complete remote access to data, management, and registration functions without any other specialized software elements. The applications may provide one or more implementations of interactive GUI's that allow the user to select from a variety of options including data selection, experiment parameters, customization features, desired visualizations, metrics and pre-filters.

In particular embodiments, the applications may be capable of running on operating systems in a non-English format, where applications may accept input from the user in various non-English language formats such as Chinese, French, Spanish, etc., and output information to the user in the same or other desired language output. For example, applications may present information to the user in various implementations of GUI in a language output desired by the user, and similarly receive input from the user in the desired language. In the present example, the applications are internationalized such that it is capable of interpreting the input from the user in the desired language where the input is acceptable input with respect to the functions and capabilities of the applications.

In particular embodiments, it may be desirable to consolidate elements of data or metadata related to an experiment, the user, or some combination thereof, to a single file that is not duplicated where duplication may sometimes be a source of error. The term "metadata" as used herein generally refers to data about data. In particular embodiments, it may also be desirable in some embodiments to restrict or prohibit the ability to overwrite data in the file. Preferentially, new information may be appended to the file rather than deleting or overwriting information, providing the benefit of traceability and data integrity (e.g. as may be required by some regulatory agencies).

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

In a particular embodiment, a system to provide notice to the operators of the cytometer lab that the samples are in transit may be conducted over the internet. U.S. Patent Publication No. 20050009078 discusses the use of internet ordering systems useful in the present invention.

Certain functional elements, such as files and data structures, may be described in the illustrated embodiments as located in system memory of a particular computer. In particular embodiments, however, they may be located on, or distributed across, computer systems or other platforms that are co-located and/or remote from each other. For example, any one or more of data files or data structures described as co-located on and "local" to a server or other computer may be located in a computer system or systems remote from the server.

In addition, it will be understood by those skilled in the relevant art that control and data flows between and among functional elements and various data structures may vary in many ways from the control and data flows described above or in documents incorporated by reference herein. More particularly, in particular embodiments, intermediary functional elements may direct control or data flows, and the functions of various elements may be combined, divided, or otherwise rearranged to allow parallel processing or for other reasons. In particular embodiments, intermediate data structures or files may be used and various described data structures or files may be combined or otherwise arranged. Numerous other embodiments, and modifications thereof, are contemplated as falling within the scope of the present invention as defined by appended claims and equivalents thereto.

Methods

Particular embodiments of the automation system perform various methods of cell preparation for multiparametric analysis on a flow cytometer. It is understood by the skilled artisan that the steps of the methods provided herein may vary in order. It is also understood, however, that while various options (of reagents, handling properties selected, or order of steps) are provided herein, the options are also each provided individually, and may each be individually segregated from the other options provided herein. Moreover, steps that are known in the art that may increase the sensitivity of the assay are intended to be within the scope of this invention. For example, there may be additional washing steps, blocking steps, etc. It is understood by the skilled artisan that steps of the methods provided herein may vary based on application, such that some steps may be added or deleted depending on the application.

FIG. 1 illustrates a high throughput system and method for high throughput flow cytometry 100. In step 101, cell samples may be prepared for processing. In step 103, cells are contacted with one or more modulators in to stimulate the cells, then the cells are fixed with a buffer containing reagent. Then the cells may be permeabilized in step 105 to allow reagent access across the cell membrane. In step 107, additional reagents are contacted with the cells to "stain" particular proteins within the cell. Thereafter, the cells are analyzed on a flow cytometer in step 109 to detect the presence or absence of the stains. See U.S. Pat. Nos. 7,381,535 and 7,393,656 or application Ser. Nos. 10/193,462; 11/655,785; 11/655,789; 11/655,821; and 11/338,957 which are all incorporated by reference in their entireties. See also 61/048,886; 61/048,920; 61/048,657; 61/079,766, and 61/085,789 which are also hereby incorporated. As illustrated in FIG. 5-FIG. 9, high through system and method for high throughput flow cytometry 100 may be utilized with a variety of applications that all result in analysis of cells on a flow cytometer, as illustrated in step 109.

The instant invention also makes use of cells that have been "potentiated." In contrast to "activation," a "potentiated" state refers the state of a cell after exposure to a modulator which then may be activated as the case may be. As described in detail below, modulators exert their effect on signaling cascades by directly or indirectly impacting the ability of an activatible protein to switch between activation isoforms.

Sample Acquisition

Many of the methods and applications described herein require samples of cells on which to perform various analyses. Cells may be acquired from variety of sources using a variety of techniques. Regardless of the collection technique used, it is important that there are a sufficient number of cells for the flow analysis. In particular embodiments, cells may be acquired from an individual, by a blood draw, a marrow draw, or a tissue extraction. In particular embodiments, cells may be acquired by a variety of other techniques and may include sources, such as bone marrow, solid tumors, ascites, washes and the like. In a particular embodiment, tissue may be taken from an individual using a surgical procedure. Surgical procedures to acquire tissue are well known in the art, as are subsequent processing of the tissue. Tissue may be fixed or unfixed, fresh or frozen, whole or disaggregated. Disaggregation of tissue may occur either mechanically or enzymatically. In particular embodiments, cells may be cultured. The cultured cells may be developed cell lines or patient derived cell lines. Procedures for cell culture are commonly known in the art.

In particular embodiments, once cell samples have been collected they may be stored for later usage, processed and stored for later usage, processed and used immediately, or simply used immediately. In particular embodiments, processing may include various methods of treatment, isolation, purification, filtration, or concentration. Particular embodiments of high throughput flow cytometry system and method may utilize fresh or cryopreserved samples of blood, bone marrow, peripheral blood, tissue, or cell cultures. Particular embodiments may utilized samples that are activated or unactivated, fixed or unfixed, lyophilized or in suspension. In a particular embodiment, processing may be performed by an automated component, such as the micropipetting assembly illustrated in FIG. 4. In a particular embodiment, an instrument may access the processing method by a computer readable tangible medium storing a computer program that contains processing instructions for various types of cell samples.

In particular embodiments, preparation of the cell samples may involve multiple steps. These steps may require multiple reagents at various times in the process and it is preferable to add the reagents soon after the blood drawing. Preferably, the reagents are added within 0, 3, 5, 10, 15, 20, 30, 45, or 50 minutes or 1, 2, 3, 4, 5, 6, 7, 8, 9, 10, 12, 15, 24, 30, or 36 hours after collection. In one embodiment, the cells are collected directly by venous puncture and treated with the reagents. See U.S. Patent Application No. 61/048,657.

In particular embodiments, blood may be treated without processing (whole blood) or may be processed in some fashion. For example, subsets of cells within the blood may be filtered and removed for further use and analysis using standard collection or filtering devices. In particular embodiments, samples may be whole blood, cell suspensions, cells in a buffy coat sample, or fixed to a solid substrate, such as a bead or plate. Some cell concentration devices or techniques may be employed by insertion between the blood collection tube and the chambers. In a particular embodiment, a filtering device that separates cells may be placed in a fluid line between the blood collection tube and another component of the system. Such devices may include micro card or lab-on-a-chip devices that separate specific subsets of cells from the whole blood. In a particular embodiment, whole blood may also be applied to filters that are engineered to contain pore sizes that select for the desired cell type or class. For example, cells may be filtered out or diluted, whole blood following the lysis of red blood cells by using filters with pore sizes between 5 to 10 μm, as disclosed in U.S. patent application Ser. No. 09/790,673. In a particular embodiment, a larger volume of blood may be necessary where the concentration of cells was low and filters may be used to concentrate the cell sample. See U.S. patent application Ser. No. 09/790,630.

Alternately, after collection of the cells, particular embodiments may place cell samples into chambers for processing through a fluid connection between the tube and the chambers See U.S. Patent Application No. 61/048,657. The fluid connection may be any one of a manner of conduits (such as commercial lab tubing) of any appropriate size and shape. Tubing is commercially available through a variety of medical and research suppliers. See the commercially available equipment from Corning, Becton-Dickinson, Sastedt, and Tygon.

Sample Processing

High throughput flow cytometry system and method is designed to facilitate automated and high throughput processing of cell samples using phosphoflow cytometry techniques.

High throughput flow cytometry system may be a flexible instrument-based system where one or more instruments may interact with each other. Furthermore, particular embodiments may integrate improved procedures to allow more samples to be analyzed in fewer steps or to provide additional information to the user. Particular embodiments may comprise several elements, such as one or more instruments, stations, or computers. Particular embodiments may be carried out by fewer elements or a single element. Additionally, any or all of the steps outlined herein may be automated. In particular embodiments, high throughput flow cytometry system may be partially or completely automated.

FIG. 1 illustrates a particular embodiment of a system and method for high throughput flow cytometry 100. In FIG. 1, system and method for high throughput flow cytometry 100 comprises islands of automation 101, 103, 105, 107, 109. In particular embodiments, any functional element of FIG. 1 may perform fewer or different operations than those described with respect to the illustrated embodiment. Also, various functional elements shown as distinct for purposes of illustration may be incorporated within other functional elements in a particular embodiment. In particular embodiments, the sequence of functions or portions of functions may be altered.

FIG. 2 illustrates a particular embodiment of a system and method for high throughput flow cytometry 200. In FIG. 2, system and method for high throughput flow cytometry 200 comprises islands of automation 201, 203, and 205. In particular embodiments, any functional element of FIG. 2 may perform fewer or different operations than those described with respect to the illustrated embodiment. Also, various functional elements shown as distinct for purposes of illustration may be incorporated within other functional elements in a particular embodiment. In particular embodiments, the sequence of functions or portions of functions may be altered.

Figure 3B:
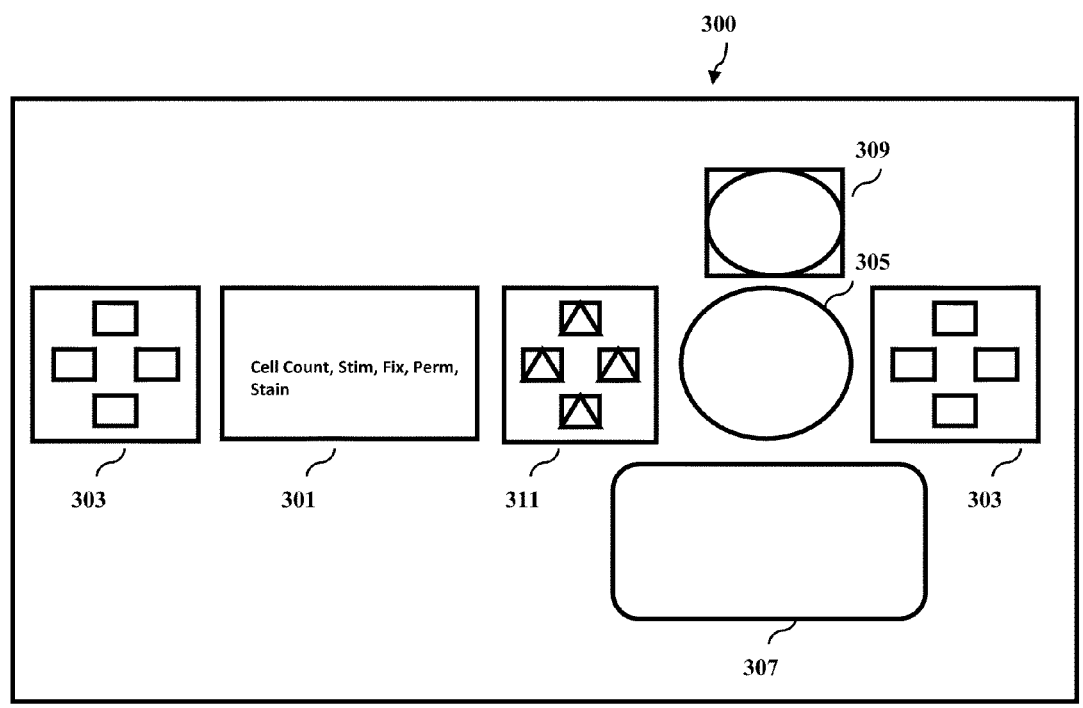
FIG. 3B illustrates a fully automated system that facilitates high-throughput processing of cell samples for phosphoflow cytometry.

FIG. 3A and FIG. 3B illustrate particular embodiments of a fully automated high throughput flow cytometry system 300 where the instrumentation is within a single platform or footprint. As will be appreciated by those in the art, there are a wide variety of components which may be used in association with the system. Components include, but are not limited to, fixed or mobile plate or reagent stages 301 with microfluidic systems; plate handlers 303 for the positioning of microplates that may have automated lid or cap handlers to remove and replace lids; one or more robotic arms 305 that may be centrally located, as illustrated in FIG. 3A, or proximately located to other components, as illustrated in FIG. 3B; flow cytometer 307; automated centrifuges 309; heated, cooled, or ambient reagent racks or stacking towers 311. Particular embodiments may have one or more of the components previously mentioned and one or more computer systems operatively linked to one or more of those components. Particular embodiments may reduce in size over time as instrumentation decreases in size or systems may be simplified as processes become more efficient. Particular embodiments may include an automated approach to inventory management in addition to pathway profiling starting from sample acquisition and ending with a full signaling pathway work-up.

Fully robotic or microfluidic systems include automated liquid-, particle-, cell- and organism-handling including high throughput pipetting and dispensing to perform all steps of screening applications. This includes liquid, particle, cell, and organism manipulations such as aspirating, dispensing, mixing, diluting, washing, accurate volumetric transfers; retrieving and discarding pipet tips; and repetitive pipetting of identical volumes for multiple deliveries from a single sample aspiration. These manipulations are cross-contamination-free liquid, particle, cell, and organism transfers. This system performs automated replication of microplate samples to filters, membranes, and/or daughter plates, high-density transfers, full-plate serial dilutions, and has high-capacity operation. In particular embodiments, robotic or microfluidic systems may manipulate any number of different reagents, including modulators, buffers, fixatives, stains, permeabilizing reagents, reagent cocktails, samples, wash solutions, assay components such as label probes, etc.

Particular embodiments of high throughput flow cytometry system may include one or more liquid handling components. The liquid handling systems themselves may include robotic systems comprising micropipetting assemblies and any number of other components, such as the components illustrated in FIG. 3A and FIG. 3B. Example instruments that may be useful include, but are not limited to, the Sciclone series i1000 or ALH3000 and its Autostacker, or the Zepher from Caliper, the Biomek series, including the $NX^P$, NX, FX and the $FX^P$ from Beckman Coulter, including the Bar Code Reading ALP, Stacker Carousel plate hotel, Cytomat conveyor ALP, Automated Tube Bar Code Reader (once microplates are formatted), or Handheld Bar Code Reader, the Velocity 11 (Agilent) series, including the BioCel, BenchCel, Bravo, and Vprep, the Tecan EVO liquid handling robots, the Platemate, Hyrdra, or Wellmate liquid handlers and dispensers from Matrix, or the Hamilton Robotics liquid handling workstations such as the STAR or STARlet Lines, or the HyperCyt Autosampler by Intellicyt or other such autosamplers. All of the above instruments are shown on the websites for the relevant companies.

Figure 4:
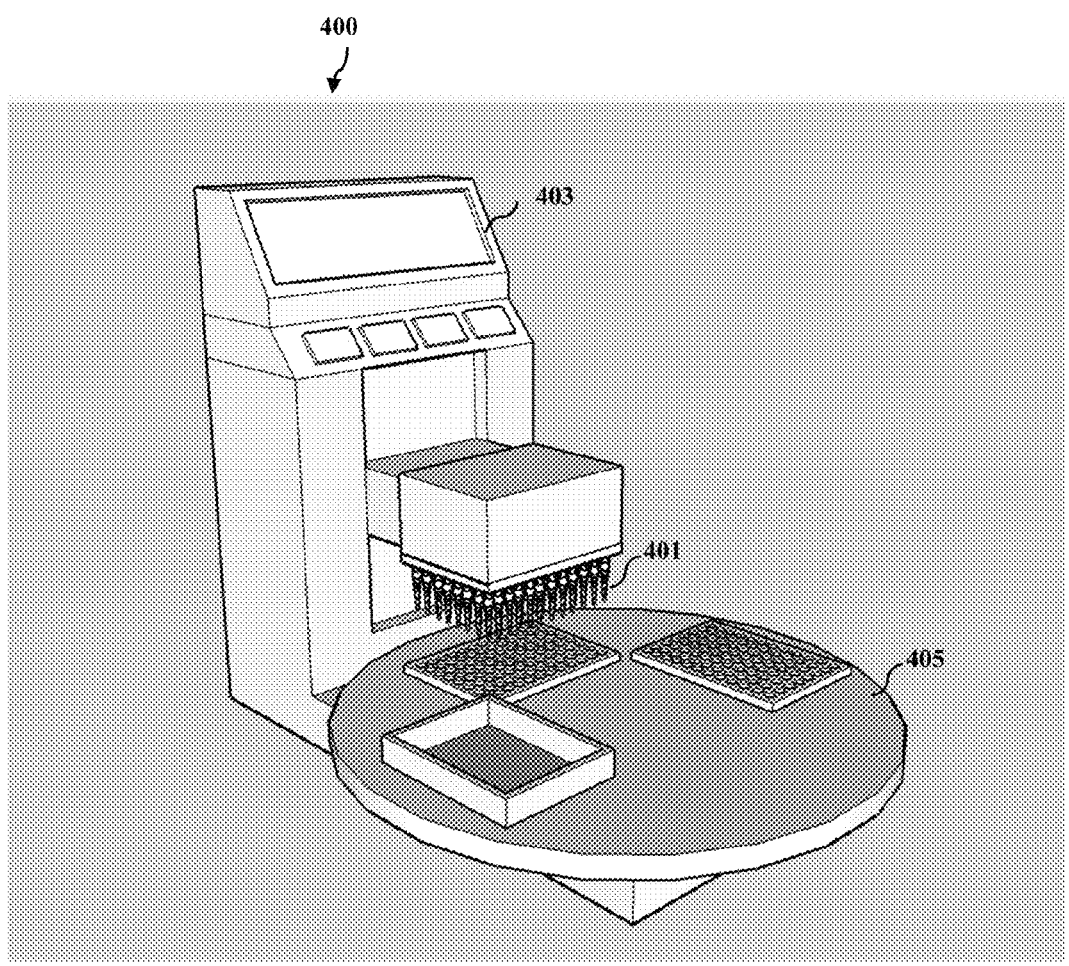
FIG. 4 illustrates an instrument for processing samples.

Micropippetting assemblies are well known in the art. See U.S. Pat. No. 6,374,683. FIG. 4 illustrates an instrument 400 with a micropipetting assembly 401, a user interface 403, a mobile plate or reagent stage 405. Instrument 400 may be a stand-alone instrument or operably linked to a computer system that contains software for instrument control and operation.

The micropipetting assembly 401 may utilize syringe, positive displacement, air displacement, peristaltic, or other dispensing technology. The micropipetting assembly 401 may use fixed or disposable tips that may be washable in a wash station. The micropipetting assembly 401 may be movable in at least two dimensions so that reagents or samples may be transferred from a container to a microplate well, from a microplate well to an alternate container, or between microplate wells. Particular embodiments of micropipetting assembly 401 may transfer liquid reagents or samples to and from microplate wells and reagent troughs. In a particular embodiment, micropipetting assembly may comprise a plurality of independently controlled micropipetters. In a particular embodiment, each micropipettor may be controlled separately for aspiration and dispense volumes, for the precise microplate wells that it will aspirate or dispense from, and for timing of such aspiration and dispenses.

User interface 403 allows an operator to manually interact with the instrument to create or execute a program to control the operation of the instrument. Mobile plate or reagent stage 405 allows micropipetting assembly 401 to interface with one or more plates or other vessels that may contain reagents or sample. In a particular embodiment, mobile plate or reagent stage 405 may include a modular platform that may accommodate heated, cooled, or ambient deck positions, a variable speed orbital shaker, positions for source and destination vessels, or sample and reagent reservoirs, pipette tips, and an active wash station. In a particular embodiment, mobile plate or reagent stage may be accessible by other components, such as a plate handler like the plate handler 305 illustrated in FIG. 3.

In particular embodiments, reagents may be delivered by a dispenser capable of aliquotting fluids to individual wells along an X-Y-Z axis. See U.S. Pat. No. 6,121,048. In particular embodiments, the dispenser may utilize a piezoelectric pump, pipettes, micropipettes, electrophoretic pumps, or mechanisms adapted from ink-jet printing technology to dispense precise amounts of fluids. In a particular embodiment, reagents may be delivered to precise locations within a plate or cartridge. In a particular embodiment, specified reactants may be delivered to certain wells which may be identified by encoded information, such as a bar code, RFID, or magnetic coding, controlled by a processor such as a computer.

Particular embodiments of high throughput flow cytometry system may include thermoregulating components. Thermoregulating components may be used to stabilize the temperature of any number of samples or reagents. Thermoregulating components may include, but are not limited to, incubators, refrigerators, freezers, heat exchangers, such as temperature controlled blocks, resistive elements, thermoelectric modules, or conductive elements. Thermoregulating components may regulate temperatures ranging from $-80°$ C. to $100°$ C. In particular embodiments, the thermoregulating component may include a temperature detection device, such as a thermocouple, which provides signals corresponding to temperature readings to another component or a computer. When a controller receives the signals corresponding to the temperature readings it may adjust the power output in order to maintain the selected temperature. In particular embodiments, thermoregulating components may be placed in close proximity to the other components for ease of access. In a particular embodiment, robotic elements, such as robotic arm 305, illustrated in FIG. 3A and FIG. 3B, may be used to transport microplates from the thermoregulating components to any other component. In a system as illustrated in FIG. 1, microplates may be transferred to and from thermoregulating components by hand from one automated component to the next.

Optionally, a temperature control mechanism such as a heater, a cooler, or a combination thereof may be disposed next to the cartridge. The temperature control mechanism may be any suitable thermally controlled element such as. The temperature control mechanism transfers heat or cold via conduction to the cartridge, which transfers heat or cold to fluid in the chamber. Alternatively, the temperature control mechanism sinks heat away from, for example, fluid in the chamber. The temperature control mechanism maintains a selected temperature in the chamber. The temperature control mechanism also Particular embodiments of high throughput flow cytometry system may utilize microtiter type plates. The plate may be conventional and commercially available, or it may be a custom design. The number of wells may be 96, 384, 1536 or other standard sizes. The volume may be as stated above, at least 1, 2, 3, 4, 5, 6, or 7 or more milliliters. Microtiter plates may be obtained from commercial suppliers such as those listed above. In a particular embodiment, the microtiter plate may have predeposited reagents.

Particular embodiments of high throughput flow cytometry system may include chemically derivatized particles, plates, cartridges, tubes, magnetic particles, or other solid phase matrix with specificity to the assay components are used. The binding surfaces of microplates, tubes or any solid phase matrices may include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a particular embodiment, plates or tubes may have preloaded reagents. In a particular embodiment, the plates may have separate wells or compartments, and each well or compartment may be capable of containing a separate reagent. These reagents may be shown in the pending U.S. applications referred to above, such as U.S. Patent Application No. 61/048,657 or 61/108,803.

Particular embodiments of high throughput flow cytometry system may include platforms for multi-well plates, multitubes, holders, cartridges, minitubes, deep-well plates, microfuge tubes, cryovials, square well plates, filters, chips, beads, and other solid-phase matrices or platforms with various volumes are accommodated on an upgradable modular platform for additional processing. Particular embodiments may include a variable speed orbital shaker, and multi-position work decks for source samples, source and destination assay plates, sample and reagent reservoirs, pipette tips, and an active wash station.

Figure 7:
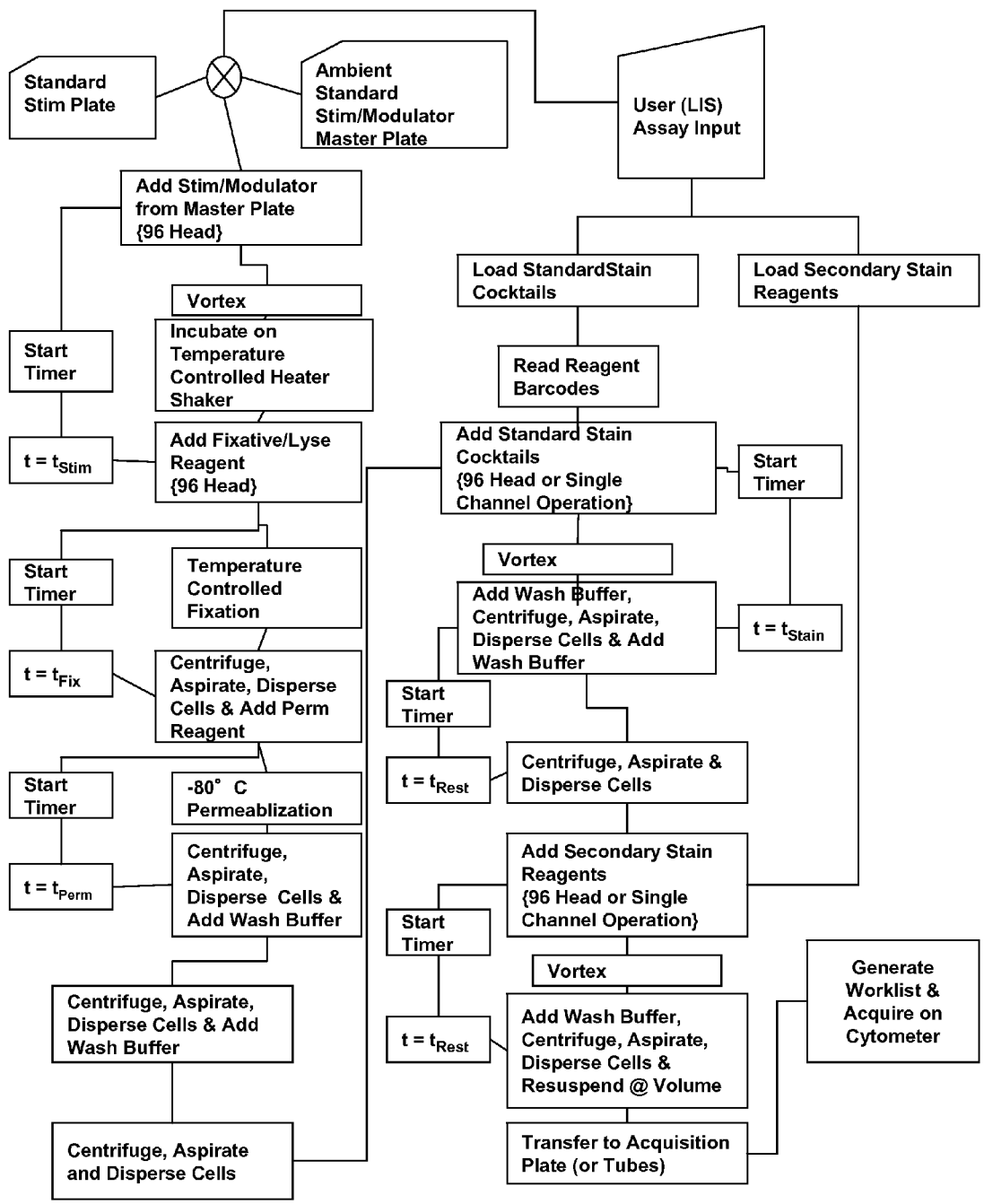
FIG. 7 illustrates an example cell stimulation assays method.

Particular embodiments of the system may use components of an automated handling apparatus similar to the simplified schematic perspective drawing in FIG. 7 of U.S. Pat. No. 7,314,595. Example components include a microplate carousel optionally situated within environmental control chamber. In some embodiments, one or more environmental control chambers may also be provided for other components. Temperatures for the chambers may range from a low of $-80°$ C., $-20°$ C., or $4°$ C. to higher temperatures of $30°$ C., $60°$ C., $95°$ C. or $100°$ C. In particular embodiments, the carousel and chamber may be structurally connected to other components by a frame. In a particular embodiment, a microplate robot may selectively move a microplate stored in slots of carousel to a microplate retainer by employing aspects of sensors and motors/actuators under control of executables. In a particular embodiment, an operator may manually place or remove the microplates from the chambers.

Particular embodiments of the system may include components, such as the components illustrated in FIGS. 11-12 of U.S. Pat. No. 7,314,595. For example, FIG. 11 illustrates a robot that contains mechanisms for holding a microplate, removing its lid, and identifying the microplate by reading a one- or two-dimensional barcode or employing any of various other machine-readable indicators (e.g., signal transmitter or transducer, or other device, any one or more of which are referred to for convenience herein simply with reference to "barcode") known to those of ordinary skill in the relevant art. In a particular embodiment the robot may also return a microplate to the carousel after it has been used, although microplates that have been processed may also be stored elsewhere. In a particular embodiment, the robot may not need to remove the lid prior to scanning the barcode or it may return it to an alternate position within the instrument other than the carousel or plate stacker. In a particular embodiment, an operator may manually scan the microplate or barcodes using a handheld barcode scanner.

Particular embodiments of the system may include microplate retainers, such as those illustrated in FIGS. 15A-C and 16A-C of U.S. Pat. No. 7,314,595. In a particular embodiment, the microplate retainer may utilize fiducial features for registering bottom surfaces of the microplates to a retainer. (See also aspects of the use of reference marks and other features and techniques as described in U.S. Pat. No. 6,121,048, hereby incorporated herein by reference in its entirety for all purposes.)

In particular embodiments, once a microplate is secured in a retainer, sampling equipment may be lowered into selected or predetermined microplate wells to add or remove reagents, cells or other reactants. In particular embodiments, the equipment may be entirely submerged in the fluid material in the microplate well. In particular embodiments, the equipment may either be kept stationery while the microplate is moved to the equipment or move to where the microplate is situated. The fluid volume in the equipment may be 0.001, 0.005, 0.01, 0.1, 0.5, 1, 2, 3, 4, 5, 6, 7, 8, 9, 10 or more microliters, but usually not more than 10, 7.5, 5.0, 2.5 or 1.0 milliliters.

In particular embodiments of the system, flexible hardware and software may allow instruments to be adaptable for multiple applications. In a particular embodiment, the software program modules may allow creation, modification, and running of one or more methods. In a particular embodiment, the system diagnostic modules may allow for instrument alignment, correct connections, and motor operations. Additionally, customized tools, labware, and liquid, particle, cell and organism transfer patterns may allow different applications to be performed. In a particular embodiment, the database may allow method and parameter storage, as well as sample tracking or additional system controls. In a particular embodiment, robotic and computer interfaces may allow communication between one or more instruments and LIMS or LIS. U.S. Patent Application Nos. 61/079,551 and 61/153,627 illustrate example interfaces that are capable of storing experimental designs, plate layout, and inventory management, and are hereby incorporated by reference in their entirety. In a particular embodiment, the method may be implemented through one or more instruments accessed by a computer readable tangible medium storing a computer program implementing the method's functionality.

Particular embodiments of high throughput flow cytometry system and method may include a system for automated processing in small volumes using a sample processing cartridge. Typical reaction volumes in a sample processing cartridge may be 1 µl to 100 ml. Particular embodiments are capable of distributing specified and accurate liquid volumes to the selected chambers. Appropriate electronic and manual valve devices may be used to ensure that liquid is placed in the correct chambers. For example, the micropipetting assemblies recited above may be used to measure liquid volumes. Valves may include standard physical devices that are present on laboratory equipment that rotate with manual stopcocks or electronic valves, or may include the types of valves or liquid shunting devices or methods that are present with lab-on-a-chip type devices where liquid volumes may be transferred to selected chambers using positive or negative pressures or other valving. See for example U.S. Pat. No. 6,830,936 and U.S. Publication Nos. 2007157973; 20060258019; 20020079008; 20060134599; and 20020125139. See also Seiler, K. et al., "Electroosmotic Pumping and Valveless Control of Fluid Flow Within a Manifold of Capillaries on a Glass Chip," Anal. Chem. 66:3485-3491 (1994); Cheng X, Irimia, et. al., Practical label-free CD4+ T cell counting of HIV-infected subjects: A Microchip approach. Lab on a Chip 2007; 10:1039; Demirci U, Toner M., Direct etch method for microfluidic channel and nanoheight post-fabrication by picoliter droplets, Applied Physics Letters 2006; 88 (5), 053117; and Irimia D, Geba D, Toner M., Universal microfluidic gradient generator, Analytical Chemistry 2006; 78: 3472-3477.

In particular embodiments, if the cells of interest were concentrated, then smaller volume cartridges may be used, such as the lab-on-a-chip devices, referred to above. For cartridges that are used in these devices a typical cartridge may be about 0.5 to 3" wide, 0.5 to 4" long, and 0.1 to 1" high or more preferably 1 to 2" wide, 1 to 3" long, and 0.5 to 1" high. Preferably, the cartridge is of sufficient size to accommodate identification labels, RFIDs, or bar codes in addition to the chambers. Cartridges in which the chambers have a volume of between 2 and 10 mls, may be between 2 to 10" wide, 2 to 12" long, and 1 to 3" high, or more preferably 5 and 9" wide, 3 and 9" long, and 1 to 2" high.

In particular embodiments, the chamber of a cartridge may have any conceivable size, shape, or orientation. Preferably, the chamber has a volume sufficient to allow the cells to contact one or more reagents, such as a modulator, and then be mixed with other reagents, like a fixative, permeabilizing reagent or a stain. In a particular embodiment, the chamber may be at least 0.2" wide, 0.2" long, and 0.2" deep. For small volume chambers the volume may be in the microliter scale, such as the volumes described above.

In particular embodiments, the cartridge may be open on two or more ends or access points. In a particular embodiment, the cell sample may be inserted through an inlet, port or opening. In a particular embodiment, there may be only one opening to insert the cell sample if the appropriate reagents are pre-deposited in the chambers awaiting cells. In a particular embodiment, the cartridge may be constructed to be able to open it to insert the sample and then to close it to incubate or otherwise mix the sample plus the reagents. In a particular embodiment, the cartridge may have a separate access point to add the reagents to the cell sample after the sample has been inserted into the chamber. The reagents may be added individually or in one operation.

In particular embodiments, a separate device, such as an automated dispenser may add reagents to the cartridge. In particular embodiments, the automated dispenser may be attached to the cartridge through a cassette. The use of a cassette having areas that align to the chambers of the cartridge may further enable high-throughput processing of the samples in lieu of the slower process of individual addition. In particular embodiments, alignment marks and structures may be added to facilitate an appropriate match between the cartridge and devices with the reagents. Alternatively, the reagents may be added to the chambers in the cartridge through the manifold opening once the manifold is removed.

In particular embodiments, selected fluids may be introduced into and out of the chamber via inlets. In particular embodiments, the inlets are located at opposite ends of the chamber. Having inlets located at opposite ends of the chamber may improve fluid circulation and regulation of bubble formation in the chamber for mixing. In a particular embodiment, the bubbles may be used to agitate the fluid, thus increasing the contact between the one or more modulators and cell samples. Other methods to mix the sample are known in the art. In a particular embodiment, inlets are located at the top and bottom end of the chamber at opposite corners. Locating the inlet at the highest and lowest positions in the chamber may facilitate the removal of bubbles from the chamber if desired. In particular embodiments, internal structure may also be used in the chamber to facilitate mixing. Such structure may be pegs, posts, or other physical structure that may disrupt the fluid flow to enhance mixing.

In particular embodiments, the cartridge may contain chambers having an inlet for the cell sample and a separate inlet for the reagents. In a particular embodiment, the reagents may be added by attaching a structure with or without its own chamber, which may align the reagents with the chambers for contact with the cells. In a particular embodiment, the structure may also have a connection to add further reagents according to a particular timed schedule as shown in the patent applications identified above.

In particular embodiments, once the first reagent is added, the cells and the fluid in the chamber may be subject to agitation to improve contact of the all of the reagents with the cells. See U.S. Pat. No. 6,399,365 for examples of agitation systems. The agitation may involve external shaking or internal fluid circulation. Ports or inlet may be used to add further reagents. In particular embodiments, during any of these procedures, the manifold may be removed and the chamber openings may be covered with a seal to prevent leakage and evaporation. The cover (or any other seal) may be attached via clips, clamps, screws, adhesives, and other fasteners.

In particular embodiments, the cartridge may include a seal at any opening of the chamber. In a particular embodiment, the seal may be a septum composed of rubber, teflon/rubber laminate, or other sealing material. The septum may be of the type commonly used to seal and reseal vessels when a needle is inserted into the septum for addition/removal of fluids. The septums, when seated in the depressions, extend slightly above surface, which in some embodiments is about 0.01" to 0.05".

It should be noted that the even distribution of fluid flow through the chamber prevents dead zones from occurring in the chamber. For example, the even distribution of fluid through the chamber substantially prevents fluid from becoming substantially quiescent at certain locations. It should also be noted that any of the components mentioned above may be used in conjunction with the cartridge.

Timing

In particular embodiments, the system may control the timings for sample handling, reagent addition, and incubation. For any given sample being processed, there may be appropriate timings for sample handling, reagent addition, and incubation, which may ensure data integrity and ease data analysis. In particular embodiments, timings for sample handling, reagent addition, and incubation may either be a very specific set time, for example, a fixative may need to incubate for exactly 10 minutes, or a range of acceptable times, for example, a stain may incubate a few hours to overnight, producing acceptable results. In a particular embodiment, the system may treat each sample the same in terms of timings at each step of the automated process for sample handling, reagent addition, and incubation.

Particular embodiments of the system may control timing in a variety of ways. In a particular embodiment, where the system is fully automated, the timing may be controlled by software, instruments, or other auxiliary systems. In a particular embodiment, the system may assure proper timing of stimulation, incubation, and fixation by using a liquid handling instrument to dispense a modulator and then a fixative into a sample while controlling the timing of all other processes as well, such as movement of the sample to shakers, incubators, hotels, or alternate positions. In a particular embodiment, where the system is not fully automated, the system may utilize human intervention, such as operator-implemented controls or batch processing to regulate the timing. In a particular embodiment of the system, each batch will proceed through the process in the same controlled manner such that each batch will be treated the same at each step of the sample preparation process within the system. The batch size may be determined by instrument limitations, limitations on sample handling, reagent addition, or incubation times, as well as overall processing time per sample or any number of other limitations imposed by the process itself to maintain data integrity.

Particular embodiments of the system may incorporate an additional method of handling appropriate timing with respect to reagent addition, such as a mechanism for timed release of reagents. Methods for timed release are known in the art and include physical structure or chemical formulations that are designed to release a reagent at a particular time after an event like adding the sample. In a particular embodiment, physical devices may include an enclosure like an ampoule that may be broken to release a reagent. In a particular embodiment, other physical devices may include structure having a porous nature that will release a reagent over time, such as a porous membrane. Examples of chemical formulations that allow the timed release of reagents include, but are not limited to micelles, liposomes, cleavable linkers attached to the reagent and/or another molecule, and the like. See U.S. Pat. Nos. 6,004,572, 5,079,005, and 5,023,080.

Particular embodiments of the system may use cartridges to prepare the samples. In a particular embodiment, an instrument to process the samples in the cartridge may control the timings for sample handling, reagent addition and incubation. In a particular embodiment, the reagents may be added to the cartridge chambers prior to the addition of the cell sample. This embodiment allows the cartridge to be preloaded and may make the process simpler for the user while still ensuring processing uniformity. In a particular embodiment, the reagents may be added after the cell samples are added to the cartridge chambers. This embodiment may require manual addition of reagents and some local processing by the operator or an instrument or mechanism that would automatically add the reagents to all chambers accurately and efficiently. Particular embodiments of the system may leave the cartridge attached or remove the cartridge and seal it from the environment.

System Controls

System controls are commonly used in the art to ease troubleshooting, maintain or improve throughput, and ensure end result data integrity. Particular embodiments of the automation system may have controls at various points within the system. Various system controls may be environmental controls, operator controls, reagent controls, instrument controls, process quality control checkpoints, and protocol controls.

In a particular embodiment, a system control for managing and monitoring the automation system may itself be a system for experimental design, layout, and inventory management. See U.S. Patent Application No. 61/079,551, which is hereby fully incorporated by reference in its entirety.

Particular embodiments of the automation system may have system controls that interface with the automation system by way of a laboratory integrated management system (LIMS) or a laboratory information system (LIS). Particular embodiments of a LIMS or LIS may be associated with a computer workstation that may contain software applications, GUI, or instruments, and may automate sample tracking from wherever the sample is initially input into the automation system through to data analysis and completion. LIMS or LIS may automate sample logging at particular process steps by communicating with one or more applications or one or more instruments. LIMS or LIS may log one or more additional information related to the plate or sample, such as a scientist or an operator, a reagent, an instrument, and a date or date and time of processing the plate or sample. A particular embodiment of LIMS or LIS may be integrated into a fully automated system. A particular embodiment of LIMS or LIS may require manual logging of one or more samples, one or more plates, one or more operators, one or more reagents, one or more instruments, one or more processing date or times or where samples enter or exit specified processes.

In a particular embodiment, a system control may be the automatic titration to determine the optimal amount of binding element. In another embodiment, a system control is the use of "sample barcoding," discussed below, to quickly and efficiently determine the optimal binding element concentration, thus reducing overall stain consumption.

Reagents

As described in detail throughout, the invention provides methods, compositions, devices and kits for high throughput flow cytometry. In some embodiments, the invention provides methods, compositions, devices and kits for phosphoflow cytometry and receptor function analysis. As such, there are numerous reagents commonly known in the art to be associated with various embodiments of the invention. In particular embodiments, some reagents may be used at multiple process steps throughout sample preparation while others may be used only once. There are various reagents that may be added to the samples, plates, or chambers before or after addition of the cell sample, thus it is known in the art that the order of reagent addition may vary. Reagents may come in a variety of compositions, such as in solid (powder, lyophilized, etc.) or liquid form and may be used in the process in these various forms as well. Reagents may also be stored and used at various temperatures throughout the process.

Modulators:

Modulators, also referred to as "stims," include chemical and biological entities, and physical or environmental stimuli. Modulators can act extracellularly or intracellularly. Chemical and biological modulators may include growth factors, cytokines, neurotransmitters, adhesion molecules, hormones, small molecules, inorganic compounds, polynucleotides, antibodies, natural compounds, lectins, lactones, chemotherapeutic agents, biological response modifiers, carbohydrate, proteases and free radicals. Physical and environmental stimuli may include electromagnetic or particulate radiation, redox potential and pH, the presence or absences of nutrients, changes in temperature, oxygen partial pressure, ion concentrations and oxidative stress. Modulators may be endogenous or exogenous and may produce different effects depending on the concentration and duration of exposure to the single cells or whether they are used in combination or sequentially with other modulators.

In particular embodiments, the modulators may include ligands for cell surface receptors (for example the modulators include IL-2, EGF, GMCSF, etc). Examples of such receptor elements include compounds or events that will activate hormone receptors, cytokine receptors, steroid receptors, adhesion receptors and growth factor receptors, including, but not limited to, PDGF-R (platelet derived growth factor receptor), EGF-R (epidermal growth factor receptor), VEGF-R (vascular endothelial growth factor), uPAR (urokinase plasminogen activator receptor), ACHR (acetylcholine receptor), IgE-R (immunoglobulin E receptor), estrogen receptor, thyroid hormone receptor, integrin receptors ($\beta 1$, $\beta 2$, $\beta 3$, $\beta 4$, $\beta 5$, $\beta 6$, $\alpha 1$, $\alpha 2$, $\alpha 3$, $\alpha 4$, $\alpha 5$, $\alpha 6$), MAC-1 ($\beta 2$ and cd11b), $\alpha V\beta 33$, opioid receptors (mu and kappa), FC receptors, serotonin receptors (5-HT, 5-HT6, 5-HT7), $\beta$-adrenergic receptors, insulin receptor, leptin receptor, TNF receptor (tissue-necrosis factor), cytokine receptors (IL1-a, IL-b, IL-2, IL-3, IL-4, IL-5, IL-6, IL-7, IL-8, IL-9, IL-10. IL-12, IL-15, IL-18, IL-21, CCR5, CCR7, CXCR4, CCR-1-10, CCL20), statin receptors, FAS receptor, BAFF receptor, FLT3 receptor, GMCSF receptor, and fibronectin receptor. Specifically contemplated are modulators that specifically relate to any of the particular receptors noted above, such as IL-2 for the IL-2 receptor, and VEGF-R for the VEGF receptor, for example.

Commercially available modulators are: Phorbol 12-Myristate 13-Acetate (PMA); Thapsigargin, Lipopolysacharride (LPS), CD40L, SCF, IGF-1, IL-6, IL-10, Etoposide, IL-3, SDF-1a/CXCL12, HydroxyUrea, Z-VAD-FMK Caspase Inhibitor, G-CSF, Erythropoetin (EPO), SDF-1B/CXCL12, IL-27, M-CSF, GM-CSF, FLT-3 Ligand, VEGF, and TRAIL.

Other modulators may be selected from the group consisting of $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, $\beta$-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, $\alpha$-Bromo-4-hydroxyacetophenone, 4-Hydroxyphenacyl Br, $\alpha$-Bromo-4-methoxyacetophenone, 4-Methoxyphenacyl Br, $\alpha$-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, and Aluminium fluoride.

Inhibitors:

Inhibitors specifically prevent a specific type of cellular activity. Phosphatase inhibitors prevent the phosphatase enzyme from removing a phosphate group from a substrate, and thus preventing a specific cellular activity. Phosphatase inhibitors may be used to analyze potential response to treatment or analyze non-response to treatment. Inhibitors may be used to correlate the expression or transporter proteins with their functionality. Inhibitors may be used to make correlations within subpopulations of cells gated both for phenotypic markers denoting stages of development along hematopoietic and lymphoid lineages, as well as reagents that recognize the transporter proteins themselves.

Inhibitors may include, but are not limited to, 3 mM hydrogen peroxide ($H_2O_2$), 3 mM $H_2O_2$+SCF and 3 mM $H_2O_2$+IFN$\alpha$, PSC833, cyclosporine, probenecid, fumitremorgin C, Ko143, and reserpine.

Fixatives:

Particular embodiments of the system may utilize assay and screening methods, such as include "fixing." Fixing may be performed to preserve or "freeze" a cell in a certain state, preferably so that an accurate representation of the structure of the cell is maintained. In particular embodiments it may be desirable to fix a cell to maintain the cell's original size and shape, to minimize loss of cellular materials, and/or to retain the reactivity and/or status of the cell's intracellular constituents (for example, the cell's phosphorylation level).

In particular embodiments, cells may be fixed by any of a variety of suitable chemical and physical methods. In a particular embodiment, fixatives may be applied to the detection of both surface and intracellular antigens. In a particular embodiment, a fixing method may be compatible with multiwell plate format assays. In a particular embodiment, one or more fixing agents may be added to cells contained in the well of an assay plate. Cells may be incubated in the presence of the fixing agent at a certain temperature (for example at room temperature, i.e., between 18° C. and 25° C.) and for a certain period of time (for example between 5 and 10 minutes). In a particular embodiment, fixation of cells in whole blood preferably would hypotonically lyse the red blood cells while simultaneously fixing and preserving the white blood cells.

An example whole blood fixative may be found here: http://www.bdbiosciences.com/external_files/pm/doc/tds/cell_bio/live/web_enabled/558049.pdf. In particular embodiments, excess fixing agent may be removed after centrifugation by aspiration of the supernatant.

Particular embodiments of the system may rely on crosslinking and/or rapid dehydration agents, such as formaldehyde, paraformaldehyde, glutaraldehyde, acetic acid, methanol, ethanol, and acetone to fix the cells. In a particular embodiment, Ortho PERMEAFIX™, or PERMIFLOW™ (INVIRION, INC.™ MI) may be used as a fixative. In a particular embodiment, a fixative may comprise 0.756%-0.85% formaldehyde, 25.4-30 mM DNBS, 6.9-6.92% DMSO and 0.086-0.095% TWEEN™ 20 detergent, although many variations may also be used.

In particular embodiments, wash buffers may be used to "fix" a cell after stimulation with a modulator. Wash buffers are know in the art. See for example, U.S. Pat. No. 7,326,577 and U.S. Publication No. 2006/0141549, which are hereby incorporated by reference in its entireties.

Particular embodiments may utilize fixatives or fixing methods described in the following references: Francis C. Connelly M C, Rapid single-step method for flow cytometric detection of surface and intracellular antigens using whole blood, Cytometry. 1996 Sep. 1; 25(1):58-70; Jacobberger, J W, Flow Cytometric Analysis of Intracellular Protein Epitopes. Immunophenotyping 2000; 361-409; S & Cheta N, Permeafix: a useful tool to detect antigens and DNA in flow cytometry, Rom J Intern Med. 1997 January-December; 35(1-4):133-5; Pizzolo G, et al. Detection of membrane and intracellular antigens by flow cytometry following ORTHO PermeaFix fixation. Leukemia. 1994 April; 8(4):672-6; Pizzolo, G, et al., Detection of membrane and intracellular antigens by flow cytometry following ORTHO PermeaFix fixation. Leukemia. 1994 April; 8(4):672-6); Metso, T, et al., Identification of intracellular markers in induced sputum and bronchoalveolar lavage samples in patients with respiratory disorders and healthy persons. Respir Med. 2002 November; 96(11):918-26); U.S. Pat. No. 5,422,277 and U.S. Pat. No. 5,597,688.

Permeabilization:

Particular embodiments of the system may "permeabilize" cells once the cells have been fixed. Permeabilization may be performed to facilitate access to cellular cytoplasm or intracellular molecules, components or structures of a cell. In particular, permeabilization may allow an agent (such as a phospho-selective antibody) to enter into a cell and reach a concentration within the cell that is greater than that which would normally penetrate into the cell in the absence of such permeabilizing treatment. In particular embodiments, cells may be stored following permeabilization or combined with labeled binding elements and then analyzed. In a particular embodiment, cells may be permeabilized in the presence of 90% methanol and incubated on ice for 30 minutes. Following this treatment, the assay plate may be stored at −20° C. for prior to being analyzed.

In particular embodiments, permeabilization of the cells may be performed by any suitable method. Selection of an appropriate permeabilizing agent and optimization of the incubation conditions and time may easily be performed by one of ordinary skill in the art. See for example, C. A. Goncalves et al., Neurochem. Res. 2000, 25: 885-894. Suitable methods include, but are not limited to, exposure to a detergent (such as CHAPS, cholic acid, deoxycholic acid, digitonin, n-dodecyl-.beta.-D-maltoside, lauryl sulfate, glycodeoxycholic acid, n-lauroylsarcosine, saponin, and triton X-100) or to an organic alcohol (such as methanol and ethanol). Other permeabilizing methods comprise the use of certain peptides or toxins that render membranes permeable. See, for example, O. Aguilera et al., FEBS Lett. 1999, 462: 273-277; and A. Bussing et al., Cytometry, 1999, 37: 133-139. Permeabilization may also be performed by addition of an organic alcohol to the cells.

Binding Element

In some embodiments of the invention, the activation level of an activatable element is determined. Thus, the methods, compositions, devices and kits of the invention may be employed to examine and profile the status of any activatable element in a cellular pathway, or collections of such activatable elements. Activatable elements include intracellular or extracellular biomolecules such as proteins, RNA, DNA, carbohydrates, metabolites, and the like. Activatable elements are described in U.S. application Ser. No. 12/460,029 filed Jul. 10, 2009; Ser. No. 12/432,720 filed Apr. 29, 2009; and Ser. No. 12/229,476 filed Aug. 21, 2008, incorporated herein by reference in their entirety. Single or multiple distinct pathways may be profiled (sequentially or simultaneously), or subsets of activatable elements within a single pathway or across multiple pathways may be examined (again, sequentially or simultaneously). As will be appreciated by those in the art, a wide variety of activation events can find use in the present invention. In general, the basic requirement is that the activation results in a change in the activatable protein that is detectable by some indication (termed an "activation state indicator"), preferably by altered binding of a labeled binding element or by changes in detectable biological activities (e.g., the activated state has an enzymatic activity which can be measured and compared to a lack of activity in the non-activated state). However, in other instances an activatable element gets activated by increase expression. Thus, in those instances the increase expression of the activatable element will be measured whether or not there is a moiety between two or more activation states of the cells.

In general, there are a variety of ways to detect the activation state of a particular protein (i.e. activatible element). Particular embodiments of the system may utilize the state of the activatable protein itself by directly assaying the activity or lack of activity within the signaling domains. In this embodiment, for example, the two isoforms may be no activity (negative signal) versus kinase activity (measured using chromogenic substrates).

In some embodiment, the activation level of an activatable element is determined by contacting a cell with a binding element ("BE") that is specific for an activation state of the activatable element. The term "Binding element" includes any molecule, e.g., peptide, nucleic acid, small organic molecule which is capable of detecting an activation state of an activatable element over another activation state of the activatable element. Binding elements and labels for binding elements are shown in U.S. Ser. No. /048,886; 61/048,920 and 61/048,657.

In some embodiments, the binding element is a peptide, polypeptide, oligopeptide or a protein. The peptide, polypeptide, oligopeptide or protein may be made up of naturally occurring amino acids and peptide bonds, or synthetic peptidomimetic structures. Thus "amino acid", or "peptide residue", as used herein include both naturally occurring and synthetic amino acids. For example, homo-phenylalanine, citrulline and norleucine are considered amino acids for the purposes of the invention. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradation.

Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. 5218: U138 Part 2 Aug. 22, 1999, both of which are expressly incorporated by reference herein.

Particular embodiments of the system may utilize labeled binding elements, or stains, or secondary stain reagents, which bind specifically to one isoform of the protein. In some embodiments, the protein BE may be an antibody. By "antibody" herein is meant a protein consisting of one or more polypeptides substantially encoded by all or part of the recognized immunoglobulin genes. The recognized immunoglobulin genes, for example in humans, include the kappa (k), lambda (I), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. The term "antibody" includes antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Particularly preferred are full length antibodies that comprise Fc variants as described herein. The term "antibody" comprises monoclonal and polyclonal antibodies. Antibodies can be antagonists, agonists, neutralizing, inhibitory, or stimulatory.

Many antibodies, many of which are commercially available (for example, see Cell Signaling Technology's and Becton Dickinson's catalogues, the contents which are incorporated herein by reference) have been produced which specifically bind to the phosphorylated isoform of a protein but do not specifically bind to a non-phosphorylated isoform of a protein. Many such antibodies have been produced for the study of signal transducing proteins that are reversibly phosphorylated. In particular, many such antibodies have been produced which specifically bind to phosphorylated, activated isoforms of protein kinases and are sometimes referred to herein as kinase activation state antibodies or grammatical equivalents thereof. Particularly preferred antibodies for use in the present invention include: phospho-AKT Ser473 monoclonal anti-4E2, phospho-p44/42 MAP kinase (Thr202/Tyr204) monoclonal antibody, phospho-TYK2 (Tyr1054/1055) antibody, phospho-p38 MAP kinase (Thr180/Tyr182) monoclonal antibody 28B10, phospho-PKC-PAN substrate antibody, phospho-PKA-substrate, phospho-SAPK/JNK (Thr183/Tyr185) G9 monoclonal antibody, phospho-tyrosine monoclonal antibody (P-tyr-100), p44/42 MAPK, p38 MAPK, JNK/SAPK, and phospho-AKT-Thr308.

In a particular embodiment, the protein BE may be an activation state-specific antibody. Accordingly, the automation system may use the methods and compositions described to detect any particular element isoform in a sample that is antigenically detectable and antigenically distinguishable from other isoforms of the activatible element. In a particular embodiment, the system may use the activation state-specific antibodies to identify distinct signaling cascades of a subset or subpopulation of complex cell populations, and the ordering of protein activation (e.g., kinase activation) in potential signaling hierarchies.

In a particular embodiment, the BE may be a stain, where stain may also be referred to as a detectable element, label or a tag. By label is meant a molecule that can be directly (i.e., a primary label) or indirectly (i.e., a secondary label) detected. By way of example, and not by way of limitation, a label may be visualized and/or measured or otherwise identified so that its presence or absence may be known. A compound may be directly or indirectly conjugated to a label which provides a detectable signal, e.g. radioisotopes, fluorescers, enzymes, antibodies, particles such as magnetic particles, chemiluminescers, specific binding molecules, or molecules that may be detected by mass spectroscopy, etc. Specific binding molecules include pairs, such as biotin and streptavidin, digoxin and antidigoxin, etc. In particular example embodiments, labels may be optical fluorescent and chromogenic dyes including labels, label enzymes radioisotopes, and quantum dots.

Kits

Particular embodiments of the high throughput flow cytometry system and method may utilize kits. Such kits may enable the detection of activatable elements by sensitive cellular assay methods, such as IHC and flow cytometry, which are suitable for the clinical detection, prognosis, and screening of cells and tissue from patients, such as leukemia patients, having a disease involving altered pathway signaling. Particular embodiments may be compatible with clinical or research applications, a highly automated or less automated high throughput flow cytometry system, and a wide variety of instruments. Particular embodiments may be provided, marketed and/or promoted to health providers, including physicians, nurses, pharmacists, formulary officials, and the like, or be marketed directly to the consumer. Particular embodiments may include reagents for sample preparation, consumable hardware, such as plates or other vessels for carrying the reagents or providing a reaction space or pipette tips or tubing, a computer readable tangible medium storing a computer software program or software files that contain kit details and processing methods required for sample preparation, and information, such as package insert materials or literature references. Particular embodiments may be packaged in any suitable manner, but typically with all elements in a single container.

In a particular embodiment, reagents for sample preparation may include one or more of the state-specific binding elements described herein, such as phospho-specific antibodies, and modulators, fixatives, buffers, therapeutic agents, and the like.

In a particular embodiment, one or more of the state-specific binding elements may be phospho-specific antibodies specific for the proteins of interest. Examples of antibodies that may be used may be selected from the group: PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHP1, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ$_1$, PLCγ2, STAT1, STAT 3, STAT 4, STAT 5, STAT 6, FAK, p130CAS, PAKs, LIMK1/2, Hsp90, Hsp70, Hsp27, SMADs, Rel-A (p65-NFKS), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25, A/B/C, Ab1, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPs, Smac, Fodrin, Actin, Src, Lyn, Fyn, Lck, NIK, Iβl, PKCα, PKCβ, PKCγ P, βcatenin, CrkL, GSK3α, GSK3β, and FOXO.

In a particular embodiment, one or more of the phospho-specific antibodies specific for the proteins selected may be selected from the group consisting of Erk, Syk, Zap70, Lck, Btk, BLNK, Cbl, PLCγ2, Akt, RelA, p38, S6. In a particular embodiment, one or more of the phospho-specific antibodies specific for the proteins selected may be selected from the group consisting of Akt1, Akt2, Akt3, SAPK/JNK1,2,3, p38s, Erk1/2, Syk, ZAP70, Btk, BLNK, Lck, PLCγ, PLCγ2, STAT1, STAT 3, STAT 4, STAT 5, STAT 6, CREB, Lyn, p-S6, Cbl, NF-κ

In a particular embodiment, modulators may be included. In a particular embodiment, one or more modulators may be selected from the group consisting of $H_2O_2$, PMA, BAFF, April, SDF1α, CD40L, IGF-1, Imiquimod, polyCpG, IL-7, IL-6, IL-10, IL-27, IL-4, IL-2, IL-3, thapsigardin and a combination thereof.

In a particular embodiment, the state-specific binding element may be conjugated to a solid support and to detectable groups directly or indirectly. In a particular embodiment, the reagents may also include ancillary agents such as buffering agents and stabilizing agents, e.g., polysaccharides and the like. In a particular embodiment, the reagents may also include other members of the signal-producing system of which system the detectable group is a member (e.g., enzyme substrates), agents for reducing background interference in a test, control reagents, apparatus for conducting a test, and the like. In a particular embodiment, one or more therapeutic agents may be included. The kit may further comprise a software package for data analysis of the physiological status, which may include reference profiles for comparison with the test profile.

In a particular embodiment, a computer readable tangible medium, including discs, thumb drives, external hard drives, contains a computer software program or software files that contain kit details and processing methods required for sample preparation. The software may include files for a specific reaction using specific reagents. In a particular embodiment, the software may include directions for carrying out the process of reagent addition, incubation, fixing cells, and other processes described herein. In a particular embodiment, the software program or software files may govern the positioning of the instrument and the amount of time the reagents are allowed to react with the cell samples. In a particular embodiment, a computer readable tangible medium is compatible with an instrument, such as the instrument illustrated in FIG. 4.

Such kits may also comprise tools and reagents to isolate a biological specimen from an individual. The kits of the invention may also comprise tools and reagent to isolate one or more components (e.g. cytokines) from the biological specimen.

Such kits may additionally comprise one or more therapeutic agents. The kit may further comprise a software package for data analysis of the physiological status, which may include reference profiles for comparison with the test profile.

Particular embodiments may include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

"Sample Barcoding"

Particular embodiments of the automation system may be adjusted to increase the throughput through the use of a process referred to as "sample barcoding." In particular embodiments, sample barcoding may reduce or eliminate well to well variation, such as variations in staining and the resultant variation in fluorescence. In particular embodiments, sample barcoding may reduce overall antibody consumption. In particular embodiments, sample barcoding may allow multiple samples that have been processed differently to be combined into a single tube or well prior to the staining step so that all samples may be analyzed together in a single run on the flow cytometer. See *Fluorescent cell barcoding inflow cytometry allows high-throughput drug screening and signaling profiling*, Krutzik, P. and Nolan G., Nature Methods, Vol. 3 No. 5, Pgs. 361-365, May 2006; see also U.S. Patent Publication No. 20080241820, which are hereby incorporated by reference in their entirety.

In particular embodiments, sample barcoding may occur during permeabilization, where the samples are also labeled with the fluorophore barcodes. In particular embodiments, samples may be labeled with different intensities of fluorophores by treatments with varying concentrations or combinations of the reactive forms of the fluorophores, which may result in each sample having a unique fluorescence intensity signature. In particular embodiments, the use of multiple fluorophores may increase the number of different samples that may be barcoded, combined into a single well, and then analyzed together. In particular example embodiments, one fluorophore may allow 4-6 samples to be analyzed together, two fluorophores may allow 16-36 samples to be analyzed together, and three fluorophores may allow 64-216 samples to be analyzed together. The greater the number of flurophores used, the greater the number of samples that may be analyzed together. In particular embodiments, downstream analysis software may be used to deconvolute the data from the single well back into separate results for each sample using the fluorescent barcodes.

In particular embodiments, sample barcoding may replace various techniques for optimizing the amount of binding element to add to a particular sample. Binding element may be added to a single sample well or tube containing both the unstim and the stim samples, which may then be analyzed together. In particular embodiments, false positives due to an overconcentration of antibodies may be quickly and accurately identified in the unstim cells by allowing the data from the unstim and stim to be visualized together. In particular embodiments, sample barcoding may indicate whether antibody concentrations are too weak or too strong. In particular embodiments, sample barcoding may permit the analysis of small shifts in cell populations that may not otherwise be noticeable with other techniques.

In particular embodiments, sample barcoding may allow for distinction between those cells that were dead at the beginning of processing and cells that died as a result of processing. A cell sample may be treated with one or more stains that are capable of distinguishing between live and dead cells, such as an amine reactive dye. Examples of stains include, but are not limited to, Aqua, Alexa (Alexa 750 among other types of Alexa dyes), and Sytox (available from Invitrogen or eBioscience). In a particular embodiment, two or more stains may be used to detect the number of cells that lost viability after various processing steps or at various time intervals. In particular embodiments, sample barcoding may allow gating between dead cells and live cells to remove dead cells from further analysis, resulting in cells being divided into three classifications.

Sample Analysis

Particular embodiments of the system may use a system or method for high throughput sample analysis. In a particular embodiment, an instrument may be employed that provides for fast and automated sampling of microplate wells. Such an instrument may be used to take the samples at the point that they are ready to be analyzed by a flow cytometer or other detector. In a particular embodiment, an instrument may deliver samples to the flow cytometer for analysis.

An example instrument that is commercially available and may be integrated into the system is the Hypercyt (Intellicyt, Albuquerque, N. Mex.). The HyperCyt® high-throughput flow cytometry approach is to fill the sample uptake/transport line with a stream of discrete sample particle suspensions separated by an air gap, each sample suspension being approximately 2 µl or larger if necessary. Particular embodiments of the system may use 1, 3, 4, 5, 6, 7, 8, 9, 10, 15 or more microliters per sample. The entire sample stream is continuously delivered to the flow cytometer so that data from all the samples in a plate are acquired and stored in a single data file. A high resolution time parameter is also recorded during data acquisition. Temporal gaps in particle detection are created in the data stream by the passage of the air bubbles, allowing the individual particle suspensions to be distinguished and separately evaluated when plotted in conjunction with the time parameter. See U.S. Pat. No. 7,368,084; http:(slashslash)www.intellicyt.com, and http:(slashslash)www.intellicyt.com/download:(slash)SBS2007HyperCyt.pdf. In a particular embodiment, the Hypercyt instrument may be operably connected to the flow cytometer and provide a liquid connection for samples to be inserted into the cytometer at a high rate.

Data Analysis

Automated sample processing for flow cytometry analysis generates large amounts of data in various formats. Particular embodiments of the automation system contain a system for automated data analysis. In a particular embodiment, automated gating of sample data may be used to automate data analysis. U.S. Patent Application No. 61/079,579 is hereby fully incorporated by reference in its entirety. In a particular embodiment, automation system may utilize a method and system for data extraction and visualization of multiparametric data. U.S. Patent Application No. 61/079,537, hereby fully incorporated by reference in its entirety.

Applications

Applications of high throughput flow cytometry system and methods may include, but are not limited to, probing various pathways by analyzing responses to a host of stimuli, assessing the inhibition or enhancement of various signaling pathways by the additions of small compounds from a small compound library, assessing expression level and functionality of various drug transporters, or probing the signaling differences among various cancer cell lines (i.e., NCI 60 cell lines). Examples of drug transporters include, but are not limited to, glycoprotein (MDR1), MDR—associated protein and breast cancer resistance protein. In particular embodiments, automation may be used to screen the supernatants from hybridomas in order to pick the best antibody secreting cell clone. In particular embodiments, automation may be used to screen for a neutralizing or agonistic antibody to a growth factor receptor by looking for the supernatant that best augments the signaling downstream of the growth factor receptor. In particular embodiments, automation may be used to select the best cell clone secreting any protein that has a biological effect that could be measured by its downstream effect on signaling. In particular embodiments, high throughput system may be used to determine the expression and functionality of cell surface proteins prior to treatment and in response to various treatments related to cancer therapy. Particular embodiments may analyze multiple characteristics of the cell in parallel and after contact with the therapy compound.

Figure 5:
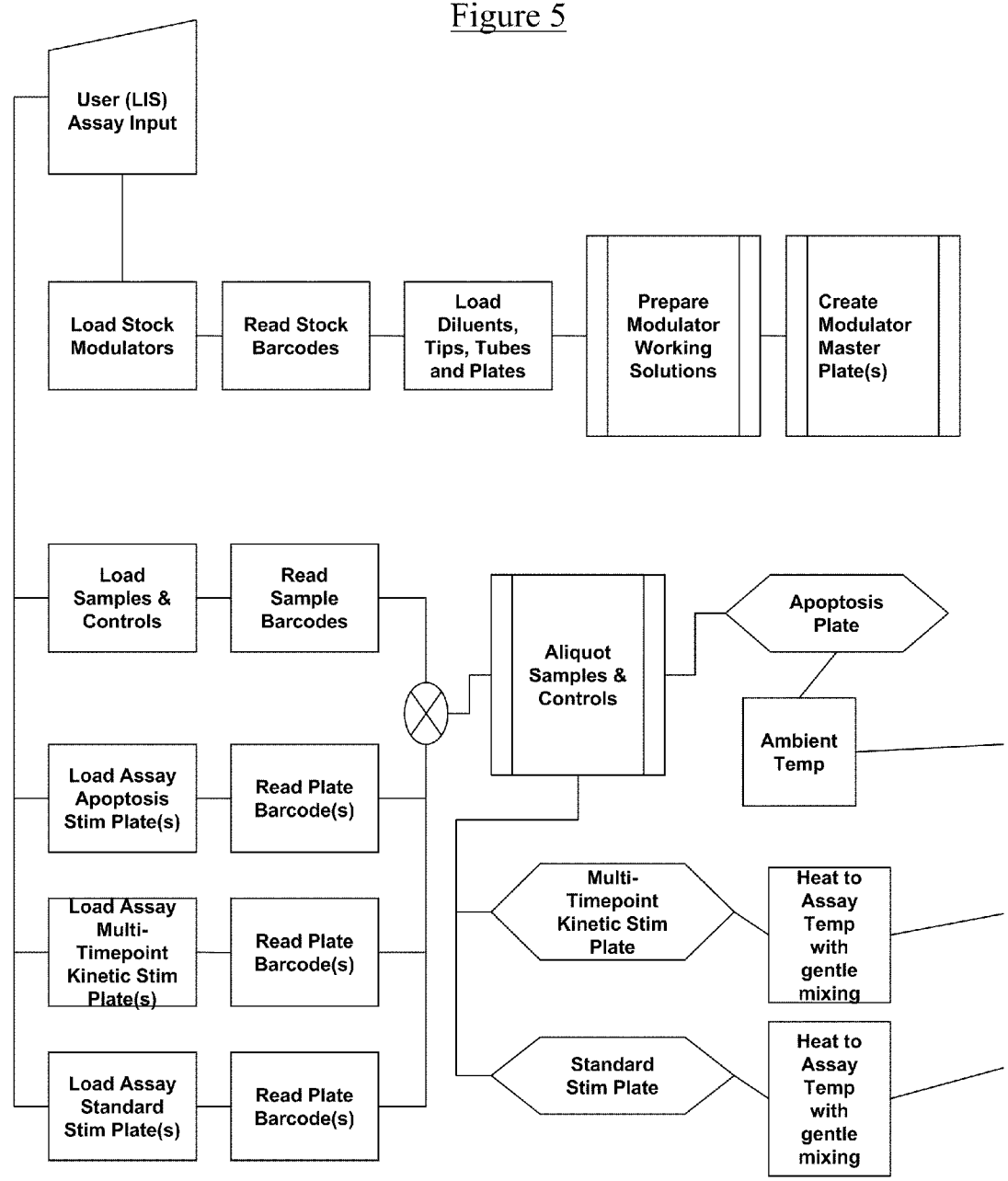
FIG. 5 illustrates an example method for sample preparation.

In particular embodiments, the system may be used for running experiments or portions of experiments including, but not limited to, apoptosis assays, cell stimulation assays, and kinetic timepoint assays. FIG. 5 illustrates an example cell sample preparation method for preparing apoptosis, standard, and kinetic timepoint plates. The following processing steps are illustrated in FIG. 5:

1. Use laboratory information system (LIS) or other automation software to initiate Liquid Handler Program.

2. System requests appropriate stock stim/modulator to be loaded.

3. System requests appropriate diluents, tips, tubes and plates for loading.

4. System loads and reads barcodes for samples, stims/modulators, tips, tubes, plates, etc.

5. System performs Stim/Modulator dilutions to create working solutions (WS) in tubes.

6. System aliquots WS into Master Stim Plates for 96 Head Stamping (All 96 wells and/or Row/Column Format).

7. System aliquots samples and controls to designated layouts in Apoptosis, Standard and Kinetic Timepoint Plates.

8. System places standard and kinetic timepoint plates on heated shakers.

a. Temperature is controlled to ±0.5° C.

b. Setpoint may be adjusted and controlled between 30° C. and 50° C.

c. Shaking/Vortex may be adjusted and controlled between 200 rpm to 1500 rpm with 3 mm amplitude 9. System logs all barcodes, source positions, volume pipetted and destination positions.

Figure 6:
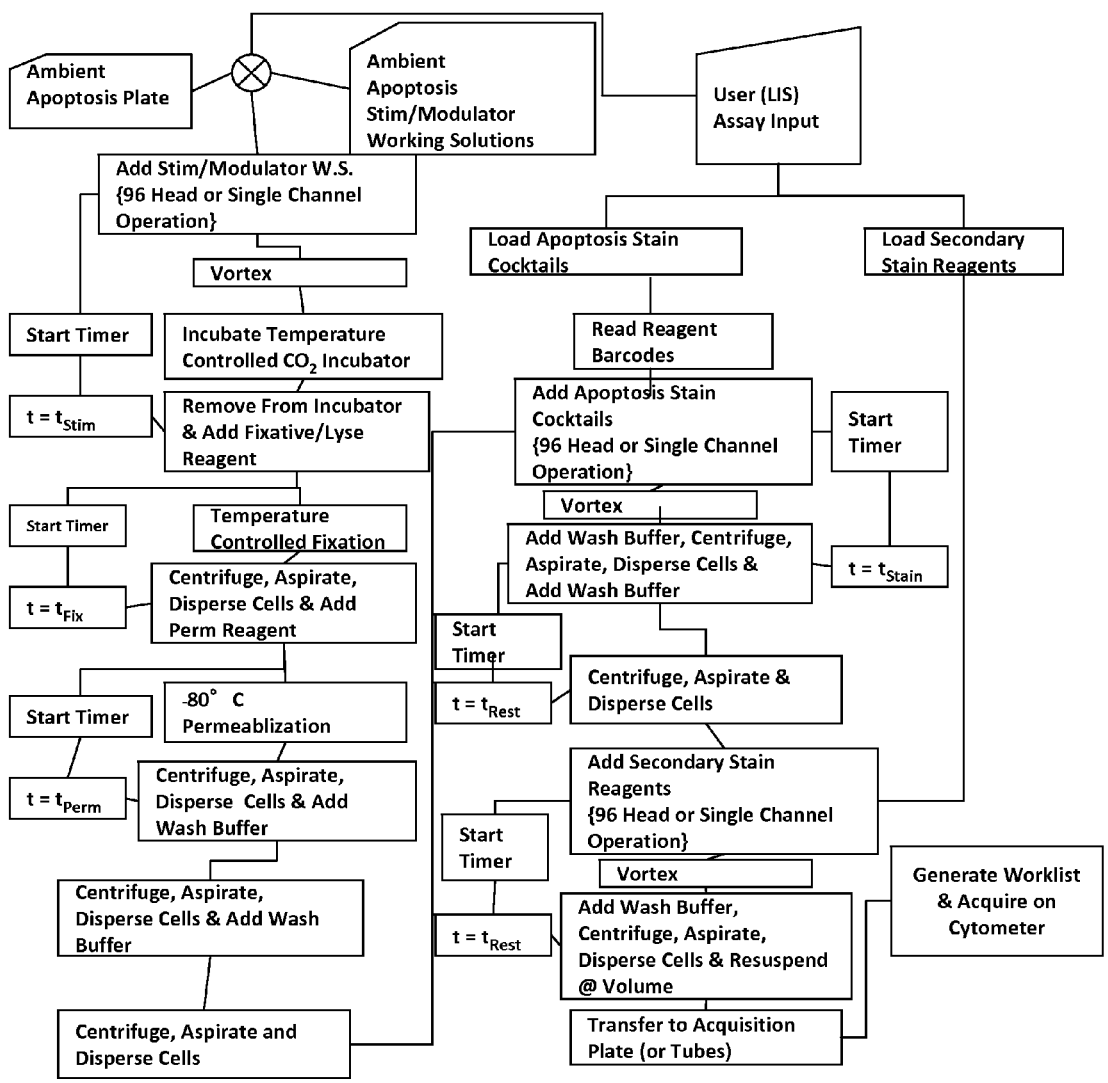
FIG. 6 illustrates an example apoptosis assays method.

FIG. 6 illustrates an example apoptosis assay method. The following processing steps are further illustrated in FIG. 6:

1. Apoptosis working solutions are pipetted according to designated format and number of samples to achieve final stim/modulator concentrations in each well. This step may require scheduling software to maintain acceptable time requirements.

2. Plate is moved to 37° C. Temperature Controlled CO2 Incubator for specified incubation time.

3. Plate is brought out of CO2 Incubator and Fix/Lyse Reagent added with temperature and time control around fixation.

4. Plate is centrifuged, aspirated and cells dispersed by vortex.

5. Permeablization Reagent is added to plate and stored for designated time at −80° C.

6. Plate is centrifuged, aspirated, cells dispersed by vortex and wash buffer added.

7. Plate is centrifuged, aspirated and cells dispersed by vortex.

8. System loads Apoptosis Stain Cocktails, pipettes to designated wells, vortexes to mix, and incubates under time and temperature control (4° C. or 25° C.).

9. Wash buffer is added, the plate is centrifuged, aspirated, cells dispersed by vortex and wash buffer added.

10. Plate incubates for set time with wash buffer.

11. Plate is centrifuged, aspirated and cells dispersed by vortex.

12. Secondary stain reagents are loaded and pipetted according to layout and number of samples.

13. Plate is incubated for set time, wash buffer added, the plate is centrifuged, aspirated, cells dispersed and resupsended to a final volume and cell concentration.

14. Samples are transferred from Deep Well to shallow well plate for acquisition (or to tube based carousel for acquisition) on cytometer.

Figure 8:
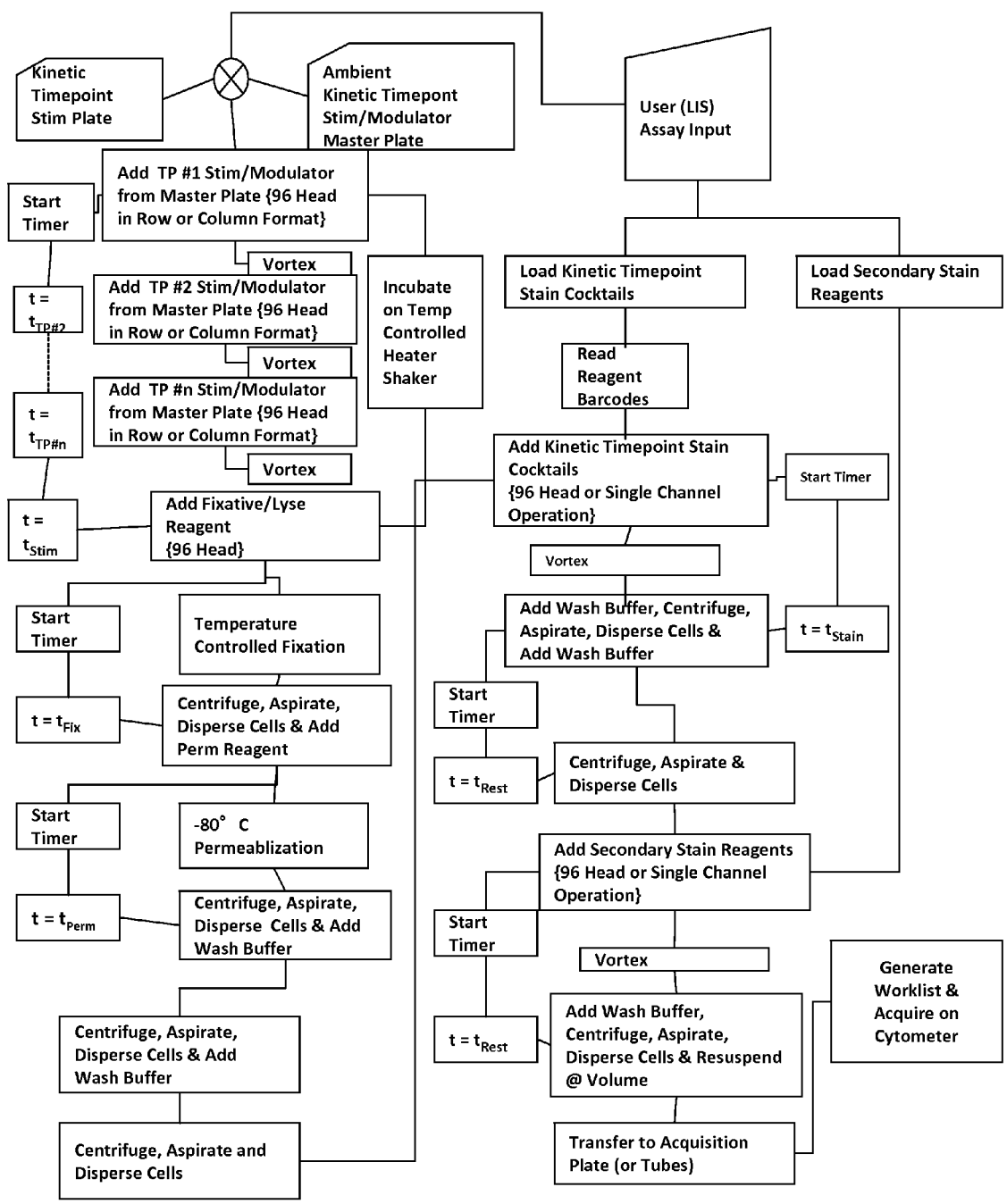
FIG. 8 illustrates an example kinetic timepoint assay method.

FIG. 7 illustrates an example standard stimulation assay method. FIG. 8 illustrates an example kinetic timepoint assay method. Processing steps for a stimulation assay method and a kinetic timepoint assay method may be similar, but may differ at the step of adding the standardized modulator working solutions or the kinetic timepoint modular working solutions respectively. The following process steps illustrate example standard stimulation and kinetic timepoint assay processing:

1. Standard Stim Plate or Kinetic Timepoint Stim Plate is moved to deep well heater/shaker and gently vortexed for predetermined time to obtain desired stimulation temperature.

2. Standardized Stim/Modulator working solutions and Kinetic Timepoint Stim/Modulator working solutions are pipetted into plate:
   a. For Standarized Stim/Modulator (as illustrated in FIG. 7): working solutions are already in desired Master Plate layout.
      i. Working solutions are pipetted by 96 Head to all wells at once.
      ii. Plate is maintained under Temperature Control on the heater/shaker for specified stim incubation time.
   b. For Kinetic Timepoint Stim/Modulator (as illustrated in FIG. 8): working solutions are already in desired Master Plate layout.
      i. At t=0, the first set of wells (rows or columns) have stim/modulator added, timer is started and the plate is vortexed briefly to assure uniform mixing and maintained at under Temperature Control on the heater/shaker for specified stim incubation time.
      ii. At an appropriate time point, the next series of stim/modulators are added, vortexed briefly to assure uniform mixing and maintained at under temperature control on the heater/shaker for specified stim incubation time. 1, 2, 3, or more iterations of this step may occur.

3. This step may require scheduling software to maintain acceptable time requirements. At designed Stim Time ($t_{stim}$), Fix/Lyse Reagent is added while maintaining temperature and time control around fixation.

4. Plate is centrifuged, aspirated and cells dispersed by vortex.

5. Perm Reagent is added to plate and stored for designated time at −80° C.

6. Plate is centrifuged, aspirated, cells dispersed by vortex and wash buffer added.

7. Plate is centrifuged, aspirated and cells dispersed by vortex.

8. System loads Standard Stain Cocktails, pipets to designated destination according to layout and number of samples, vortex to mix and incubates under time and temperature control (4° C. or 25° C.).

9. Wash buffer is added, the plate is centrifuged, aspirated, cells dispersed by vortex and wash buffer added.

10. Plate incubates for set time with wash buffer.

11. Plate is centrifuged, aspirated and cells dispersed by vortex.

12. Secondary Stain Reagents are loaded and pipetted according to layout and number of samples.

13. Plate is incubated for set time, wash buffer added, the plate is centrifuged, aspirated, cells dispersed and resupsended to a final volume and cell concentration.

14. Samples are transferred from Deep Well to shallow well plate for acquisition (or to tube based carousel for acquisition) on cytometer.

Figure 9:
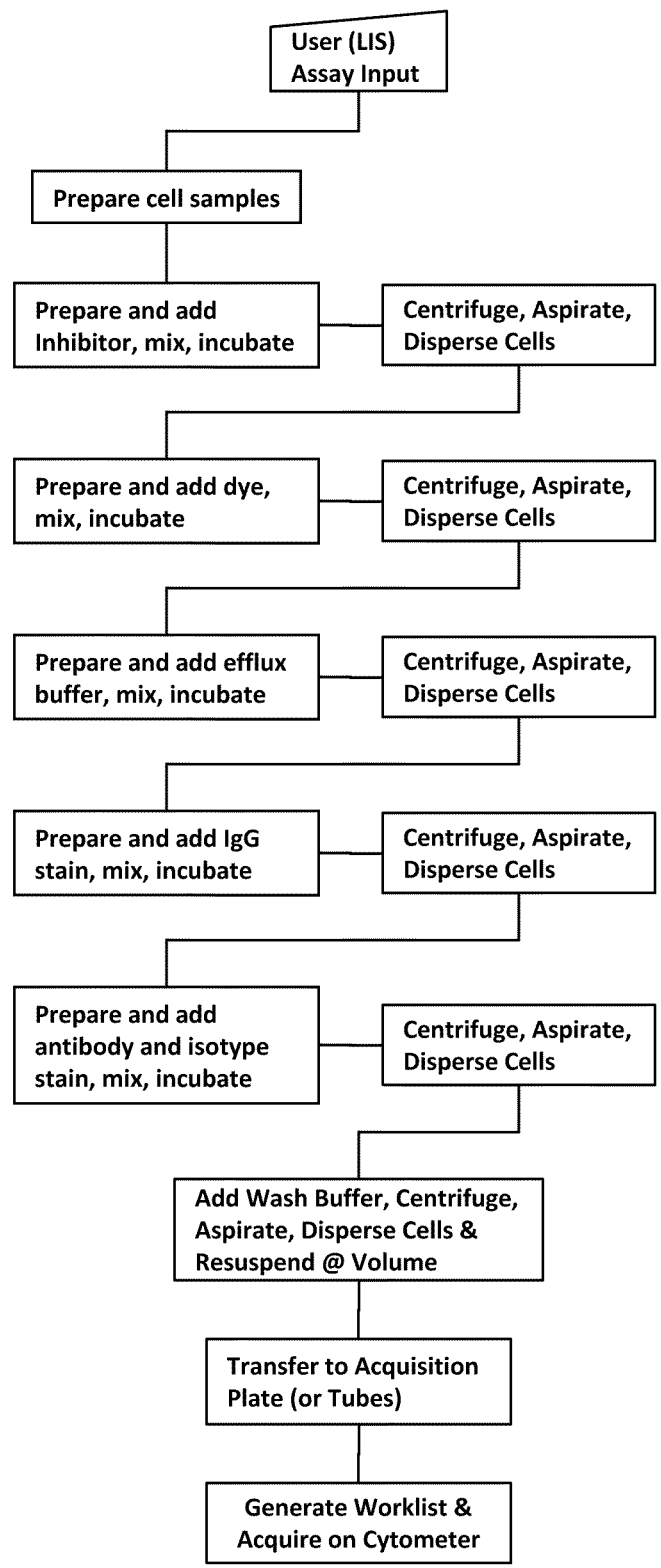
FIG. 9 illustrates an example efflux assay method.

FIG. 9 illustrates an example high throughput multi-drug resistant functional efflux assay method that may be used to determine expression and functionality of specific cell surface proteins prior to and in response to a given therapy. The following steps illustrate the high throughput multi-drug resistant functional efflux assay method of processing:

1. Use laboratory information system (LIS) or other automation software to initiate Liquid Handler Program.

2. Cell sample plates are prepared according to cell type by either thawing and resuspending, resuspending, or isolating and resuspending. RPMI 10% FCS buffer and/or RPMI 10% FBS buffer may be added to each sample as necessary.

3. Inhibitor is prepared to a specific concentration and stored at 37° C. until use.

4. Appropriate amount of inhibitor is added to sample plate, mixed, and incubated for 15 minutes at 37° C.

5. Dye solution is prepared from concentrated dye and DPBS/0.5% BSA.

6. Plates are removed from incubator 30 seconds prior to adding dye solution, and then appropriate amount of dye solution is added to sample plate, mixed, and incubated for 45 minutes at 37° C.

7. Plate is centrifuged, aspirated and cells dispersed by vortex.

8. Efflux buffer is prepared using RPMI 10% FCS.

9. Appropriate amount of efflux buffer is added to sample plate, incubated at 37° C. for 20 minutes.

10. Plate is centrifuged, aspirated and cells dispersed by vortex.

11. IgG staining solution is prepared and added to sample plate, mixed, vortexed, and incubated on ice (or equivalent temperature) for 5 minutes.

12. Plate is centrifuged, aspirated and cells dispersed by vortex.

13. Specific antibody and isotype staining mixtures are prepared and added to sample plate, mixed, vortexed, and incubated on ice (or equivalent temperature) in the dark for 30 minutes.

14. Plate is centrifuged, aspirated and cells dispersed by vortex.

15. Wash buffer is added, plate is centrifuged, aspirated, cells dispersed by vortex.

16. After final wash/aspiration, cells are dispersed and resupsended to a final volume and cell concentration.

17. Samples are transferred from Deep Well to shallow well plate for acquisition (or to tube based carousel for acquisition) on cytometer.

While preferred embodiments of the present invention have been shown and described herein, it will be obvious to those skilled in the art that such embodiments are provided by way of example only. Numerous variations, changes, and substitutions will now occur to those skilled in the art without departing from the invention. Many other schemes for distributing functions among the various functional elements of the illustrated embodiment are possible. The functions of any element may be carried out in various ways in alternative embodiments. It should be understood that various alternatives to the embodiments of the invention described herein may be employed in practicing the invention. Therefore, the present disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Thus, it is intended that the following claims define the scope of the invention and that methods and structures within the scope of these claims and their equivalents be covered thereby.

What is claimed is:

1. A method for automated processing of samples and multiparametric analysis of the processed samples in a cytometer, comprising:
    a. providing a system for processing samples to produce processed samples prior to analyzing the processed samples in the cytometer, comprising:
        1. at least one microplate and microplate holder;
        2. a first reagent container containing a first detectable binding element that is specific for an activation state of a first activatable element, a second reagent container containing a second detectable binding element that is specific for a first cell surface marker, wherein the first and second detectable binding elements are differentially detectable by the cytometer, and either a third reagent container containing a first modulator or a sample container containing a biological sample comprising cells, or both, wherein the modulator, the detectable binding elements, and the biological sample comprising cells are in liquid solution or suspension in their respective reagent containers;
        3. a dispensing head configured to withdraw liquid from one of said reagent or sample containers and dispense it to a well in said microplate, and/or to withdraw liquid from a first well in the microplate and dispense it to a second well in the same or different microplate;
        4. a microplate handling apparatus for moving said microplate, wherein:
            i. said microplate handling apparatus is configured to position said microplate near said dispensing head so that said dispensing head can dispense liquid from a reagent container into a well in said microplate and/or withdraw liquid from a well in said microplate during the production of a processed sample; and
            ii. said microplate handling apparatus is configured to either relocate said microplate to said cytometer for transfer of the processed sample to, and analysis of the processed sample by, the cytometer, or to position said microplate so that it may be relocated manually to said cytometer for transfer of the processed sample to, and analysis of the processed sample by the cytometer;
        5. a tracking mechanism, wherein the tracking mechanism is automated, manual, or a combination thereof, and wherein the tracking mechanism comprises a barcode reader, a manual input station, or a combination thereof;
    b. providing a system for analysis and management of the processed samples in step a, comprising:
        1. said cytometer, wherein the cytometer is configured to differentially detect a plurality of differentially detectable binding elements bound to activable elements and cell surface markers in single cells present in said samples; and
        2. a computer system including
            i. a processor,
            ii. a display unit,
            iii. a laboratory information management system (LIMS) configured to track and record an experiment, inventory management and experimental design and to automate sample tracking from wherever the sample is initially input into the automation system through to data analysis and completion, and
            iv. a memory unit configured to control, and operably connected to, said microplate holder, said tracking mechanism, said microplate handling apparatus, said dispensing head, and said cytometer, wherein the memory unit and the LIMS are configured to communicate with the cytometer by instrument control and image processing application software to inform the cytometer as to plate layout, including the presence or absence of the first or second differentially detectable binding elements, or combination thereof, for each well in the plate, wherein there are potentially at least 6 differentially detectable binding elements and each well of the plate may contain one or more different binding elements compared to other wells, as well as the presence or absence of one or more modulators, with corresponding modulation time, so as to direct proper analysis of each of the samples in each well of the plate by the cytometer, in a manner compatible with the cytometer software, wherein the computer system is configured to consolidate elements of data or metadata to a single file;
    c. withdrawing and dispensing liquids from said reagent containers into one or more wells of the at least one microplate to perform a protocol, wherein said protocol comprises:
        1. either:
            i. providing the at least one microplate, one or more of whose wells contains a biological sample comprising cells, and dispensing the first modulator from said third reagent container into the wells so that the first modulator and the cells are in contact; or
            ii. providing the at least one microplate, one or more of whose wells contains a first modulator and dispensing at least one biological sample comprising cells from said sample container into the wells so that the first modulator and the cells are in contact; or
            iii. providing the at least one microplate and dispensing at least one biological sample from the sample container into one or more wells of the microplate and dispensing the first modulator from the third reagent container into one or more of the wells of the microplate, so that the first modulator and the cells are in contact; and
        2. determining an activation level of at least said first activatable element in single cells in said one or more samples, wherein said first activatable element is an element in a pathway that is modulated by the first modulator, by said cytometer, wherein said activation level is determined by a process comprising:
            contacting said at least one biological sample with the first detectable binding element which is specific to an activation state of said first activatable element, wherein said contacting comprises: withdrawing said first detectable binding element from said first reagent container and dispensing said first detectable binding element to the well in the microplate containing said sample such that said first detectable binding element contacts the cells in said sample and binds to the first activatable element, if present, and detecting said bound first detectable binding element in said cells on a single cell basis in the cytometer; and 3. determining a level of at least said first cell surface marker in said one or more samples on a single cell basis by said cytometer, wherein said first cell surface marker level is determined by a process comprising: contacting said at least one biological sample with the second detectable binding element which is specific to the first cell surface marker, wherein said contacting comprises: withdrawing said second detectable binding element from said second reagent container and dispensing said second detectable binding element to the well in the microplate containing said sample such that said second detectable binding element contacts the cells in said sample and binds to said first cell surface marker, if present, and detecting said bound second detectable binding element in said cells on a single cell basis in the cytometer.

2. The method of claim 1 wherein said system for processing samples further comprises one or more reagent containers containing a buffer, a fixative, or a permeabilizer.

3. The method of claim 1, wherein the protocol of part c. further comprises fixing, or permeabilizing, the cells or a combination thereof, in the sample in the wells of the at least one microplate.

4. The method of claim 1, wherein the tracking mechanism comprises a barcode scanner and said at least one microplate further comprises a barcode.

5. The method of claim 4, further comprising scanning the barcode and associating said barcode with a microplate processing information.

6. The method of claim 1, wherein said detectable binding elements comprise an antibody, or a recombinant protein, and the binding element is rendered detectable by attachment to a fluorescent dye or a mass label.

7. The method of claim 6 wherein said activatable element is activated by phosphorylation or cleavage, and said antibody or recombinant protein is specific to a phosphorylation state or a cleavage state of said activatable element.

8. The method of claim 1, wherein said at least one microplate is a 96 well plate.

9. The method of claim 1, wherein the automated processing of samples is performed in about 1.5 hours.

10. The method of claim 1 wherein said samples comprise intact viable cells and wherein said pre-processing comprises contacting said intact viable cells with the modulator for a predetermined time, and wherein the contacting of step c.1.i., c.1.ii., or c.1.iii. further comprises contacting the cells and the modulator in such a way that the sample remains viable during the contacting for the predetermined time.

11. The method of claim 10 wherein the computer system is configured to control the contacting of the cells with the modulator for the predetermined time.

12. The method of claim 11 wherein the computer system controls the contacting of the cells with modulator for the predetermined time by controlling a process comprising fixing of the sample after treatment with the modulator.

13. The method of claim 12 wherein said process comprising fixing of the sample after treatment with the modulator comprises withdrawing the fixative from a reagent container or containers and dispensing the fixative to the wells of the at least one microplate containing the sample, or withdrawing said sample from a sample container and dispensing the sample to wells of the at least one microplate containing the fixative, such that the fixative contacts the cells of the sample.

14. The method of claim 13 wherein the computer system controls the contacting of the cells with fixative for a predetermined time.

15. The method of claim 1 wherein the method is an automated method for pathway profiling in single cells starting with said sample and ending with a full signaling pathway workup, wherein the signaling pathway comprises a pathway modulated by the modulator, further comprising d. providing a system for determining the status of a signaling pathway in the single cells, whereby an automated approach to pathway profiling starting from sample and ending with a full signaling pathway workup is provided.

16. The method of claim 1 wherein the system further comprises at least one of a fifth reagent container containing a third detectable binding element specific to an activation state of a second activatable element, a sixth reagent container containing a fourth detectable binding element specific to an activation state of a third activatable element, or a seventh reagent container containing a fifth detectable binding element specific to an activation state of a fourth activatable element, wherein the third, fourth, and fifth detectable binding elements are differentially detectable from each other and from the first and second binding elements, and wherein each detectable binding element is contacted with cells in sample in at least one well of the at least one microplate and detected by the cytometer.

17. The method of claim 16 wherein the system comprises at least two of the fifth, sixth, and seventh reagent containers and their respective detectable binding elements.

18. The method of claim 16 wherein the system comprises all three of the fifth, sixth, and seventh reagent containers and their respective detectable binding elements.

19. The method of claim 1 wherein the system further comprises at least one of an eighth reagent container containing a sixth detectable binding element that is specific to a second cell surface marker, a ninth reagent container containing a seventh detectable binding element that is specific to a third cell surface marker, or a tenth reagent container containing an eighth detectable binding element, wherein the sixth, seventh, and eighth detectable binding elements are differentially detectable from each other and from the first, second, third, fourth, and fifth binding elements, and wherein each detectable binding element is contacted with cells in sample in at least one well of the at least one microplate and detected by the cytometer.

20. The method of claim 19 wherein at least two of the first, second, fifth, sixth, seventh, eighth, ninth, and tenth reagent containers are the same reagent container, and the cells in the sample in the well of the at least one microplate that are contacted with the liquid in the container are contacted with at least two of the first, second, third, fourth, fifth, sixth, seventh, and eighth detectable binding elements and the two detectable binding elements are detected on a single cell basis by the cytometer.

21. The method of claim 19 wherein at least three of the first, second, fifth, sixth, seventh, eighth, ninth, and tenth reagent containers are the same reagent container, and the cells in the sample in the well of the at least one microplate that are contacted with the liquid in the container are contacted with at least three of the first, second, third, fourth, fifth, sixth, seventh, and eighth detectable binding elements and the three detectable binding elements are detected on a single cell basis by the cytometer.

22. The method of claim 19 wherein at least four of the first, second, fifth, sixth, seventh, eighth, ninth, and tenth reagent containers are the same reagent container and the cells in the sample in the well of the at least one microplate that are contacted with the liquid in the container are contacted with at least four of the first, second, third, fourth, fifth, sixth, seventh, and eighth detectable binding elements and the four detectable binding elements are detected on a single cell basis by the cytometer.

23. The method of claim 19 wherein at least five of the first, second, fifth, sixth, seventh, eighth, ninth, and tenth reagent containers are the same reagent container, and the cells in the sample in the well of the at least one microplate that are contacted with the liquid in the container are contacted with at least five of the first, second, third, fourth, fifth, sixth, seventh, and eighth detectable binding elements and the five detectable binding elements are detected on a single cell basis by the cytometer.

24. The method of claim 19 wherein at least six of the first, second, fifth, sixth, seventh, eighth, ninth, and tenth reagent containers are the same reagent container, and the cells in the sample in the well of the at least one microplate that are contacted with the liquid in the container are contacted with at least six of the first, second, third, fourth, fifth, sixth, seventh, and eighth detectable binding elements and the six detectable binding elements are detected on a single cell basis by the cytometer.

25. The method of claim 19 wherein the first and the second microplates are the same microplate.

26. The method of claim 1 wherein the system further comprises at least one of a reagent container containing a second modulator, a reagent container containing a third modulator, a reagent container containing a fourth modulator, a reagent container containing a fifth modulator, or a reagent container containing a sixth modulator, wherein the second, third, fourth, fifth, and sixth modulators are different from the first modulator and different from each other.

27. The method of claim 1 wherein the system further comprises at least two of a reagent container containing a second modulator, a reagent container containing a third modulator, a reagent container containing a fourth modulator, a reagent container containing a fifth modulator, or a reagent container containing a sixth modulator, wherein the second, third, fourth, fifth, and sixth modulators are different from the first modulator and different from each other.

28. The method of claim 1 wherein the system further comprises at least three of a reagent container containing a second modulator, a reagent container containing a third modulator, a reagent container containing a fourth modulator, a reagent container containing a fifth modulator, or a reagent container containing a sixth modulator, wherein the second, third, fourth, fifth, and sixth modulators are different from the first modulator and different from each other.

29. The method of claim 1 wherein the system further comprises at least four of a reagent container containing a second modulator, a reagent container containing a third modulator, a reagent container containing a fourth modulator, a reagent container containing a fifth modulator, or a reagent container containing a sixth modulator, wherein the second, third, fourth, fifth, and sixth modulators are different from the first modulator and different from each other.

30. The method of claim 1 wherein the system further comprises at least five of a reagent container containing a second modulator, a reagent container containing a third modulator, a reagent container containing a fourth modulator, a reagent container containing a fifth modulator, or a reagent container containing a sixth modulator, wherein the second, third, fourth, fifth, and sixth modulators are different from the first modulator and different from each other.

31. The method of claim 1 wherein the cytometer is a flow cytometer and the memory or LIMS, or both, communicates with the cytometer in such a manner as to allow the cytometer to determine, for each detectable binding element in each sample corresponding to a well in the at least one microtiter plate:
   i. an excitation wavelength for detection of each detectable binding element;
   ii. an emission wavelength for detection of each detectable binding element;
   iii. an extinction coefficient for quantification of each detectable binding element; or
   iv. associated power level values for each detectable binding element, or a combination thereof.

32. The method of claim 1 wherein the cytometer is the only detector for detecting cell status in the system.

33. The method of claim 1 wherein the cytometer is a flow cytometer.

34. The method of claim 1 wherein the cytometer is a mass cytometer.

35. The method of claim 1 wherein the contacting of said one or more biological samples with one or modulators of step d.(i) occurs in a first microplate, and the contacting of the biological sample with a binding element of step d.(ii) occurs in a second microplate.

36. The method of claim 1 wherein activation levels of a plurality of activable elements are determined.

37. The method of claim 1 wherein the first activatable element comprises an activatable element in an apoptosis pathway.

38. The method of claim 1 wherein all sample preparation is done in the wells of a microplate and the volume of sample in the wells does not exceed 250 microliters.

39. The method of claim 1 wherein the method is fully automated.

40. The method of claim 1 wherein the method is partially automated and partially manual.

41. The method of claim 1 wherein the single file is not duplicated.

42. A method for automated processing of samples and analysis of the processed samples by a cytometer, comprising:
   A. providing a system for processing said samples prior to their analysis in a cytometer, comprising:
      1. at least one or more microplate and microplate holder, the microplates having a barcode;
      2. a first reagent container containing a first detectable binding element that is specific for an activation state of a first activatable element, a second reagent container containing a second detectable binding element that is specific for a first cell surface marker, wherein the first and second detectable binding elements are differentially detectable, and either a third reagent container containing a first modulator or a sample container containing a biological sample comprising cells, or both, wherein the modulator, the detectable binding elements, and the biological sample comprising cells are in liquid solution or suspension in their respective reagent containers;
      3. a dispensing head configured to withdraw liquid from one of said reagent or sample containers and dispense it to a well in said microplate and/or to withdraw liquid from a first well in the microplate and dispense it to a second well in the same or different microplate;

4. a microplate handling apparatus for moving said microplate, wherein;
   i. said microplate handling apparatus is configured to position said microplate near said dispensing head so that said dispensing head can dispense liquid from a reagent container into a well in said microplate and/or withdraw liquid from a well in said microplate during the production of a processed sample; and
   ii. said microplate handling apparatus is configured to either relocate said microplate to said cytometer for transfer of the processed sample to, and analysis of the processed sample by, the cytometer, or to position said microplate so that it may be relocated manually to said cytometer for transfer of the processed sample to, and analysis of the processed sample by the cytometer; and
5. a barcode reader;
b. providing a system for, analysis and management of the processed samples in step a, comprising:
   1. said cytometer, wherein the cytometer is configured to differentially detect a plurality of differentially detectable binding elements bound to activable elements and cell surface markers in single cells present in said samples;
   2. a computer system, wherein said computer system comprises
      i. a processor,
      ii. a display unit,
      iii. a LIMS configured to track and record an experiment design and to automate sample tracking from wherever the sample is initially input into said automation process and analysis through to data analysis and completion, and
      iv. a memory unit configured to control, and operably connected to, said microplate holder, said barcode reader, said microplate handling apparatus, the timing of said microplate handling steps, said dispensing head, and said cytometer, wherein the memory unit and the LIMS are configured to communicate with the cytometer by instrument control and image processing application software to inform the cytometer as to plate layout, including the presence or absence of the first or second differentially detectable binding elements, or combination thereof, for each well in the plate, wherein there are potentially at least 6 differentially detectable binding elements and each well of the plate may contain one or more different binding elements compared to other wells, as well as the presence or absence of one or more modulators, with corresponding modulation time, so as to direct proper analysis of each of the samples in each well of the plate by the cytometer, in a manner compatible with the cytometer software, wherein the computer system is configured to consolidate elements of data or metadata to a single file;
c. withdrawing and dispensing liquids from said reagent containers into one or more wells of the at least one microplate to perform a protocol, wherein said protocol comprises:
   1. either:
      i. providing the at least one microplate, one or more of whose wells contains biological sample comprising cells, and dispensing modulator from said third reagent container into the wells so that the modulator and the cells are in contact; or
      ii. providing the at least one microplate, one or more of whose wells contains a modulator and dispensing at least one biological sample comprising cells from said sample container into the wells so that the modulator and the cells are in contact; or
      iii. providing the at least one microplate and dispensing at least one biological sample from the sample container into one or more wells of the microplate and dispensing modulator from the third reagent container into one or more of the wells of the microplate, so that the modulator and the cells are in contact; and
   2. contacting said samples with a fixative and a permeablization reagent;
   3. determining an activation level of at least said first activatable element in single cells in said one or more samples wherein said first activatable element is an element in a pathway that is modulated by the modulator, by said cytometer, wherein said activation level is determined by a process comprising:
      contacting said at least one biological sample with the first detectable binding element which is specific to an activation state of said first activatable element, wherein said contacting comprises: withdrawing said first detectable binding element from said first reagent container and dispensing said first detectable binding element to the well in the microplate containing said sample such that said first detectable binding element contacts the cells in said sample and binds to the first activatable element, if present, and detecting said bound first detectable binding element in said cells on a single cell basis in the cytometer;
   4. determining a level of at least said first cell surface marker in said one or more samples on a single cell basis by said cytometer, wherein said first cell surface marker level is determined by a process comprising: contacting said at least one biological sample with the second detectable binding element which is specific to the first cell surface marker, wherein said contacting comprises: withdrawing said second detectable binding element from said second reagent container and dispensing said second detectable binding element to the well in the microplate containing said sample such that said second detectable binding element contacts the cells in said sample and binds to said first cell surface marker, if present, and detecting said bound second detectable binding element in said cells on a single cell basis in the cytometer;
d. wherein the LIMS software is configured to direct experimental design, plate layout, sample tracking, and inventory management and one or more of the following purposes from the group consisting of instrument alignment; correct connections; motor operations; timing for sample handling; and data analysis.

43. The method of claim 42, further comprising: reading the barcode; and using software to select reagents and equipment for sample processing based on the barcode.

44. The method of claim 42, wherein the steps in the protocol are conducted in islands of automation.

45. The method of claim 42, wherein one or more components of the system are in a thermo regulating component.

46. The method of claim 42, wherein the microplate handling apparatus comprises a robotic arm, and further comprising moving the at least one microplate using the robotic arm.

47. The method of claim 42, further comprising controlling the temperature during one or more steps in the process.

48. The method of claim 42, further comprising providing an instrument to agitate the samples in the at least one microplate.

49. A method for automated processing of samples and multiparametric analysis of the processed samples in a cytometer, comprising:
- a. providing a system for processing samples to produce processed samples prior to analyzing the processed samples in a cytometer, comprising:
  1. at least one microplate and microplate holder;
  2. a first reagent container-containing a first detectable binding element that is specific for an activation state of a first activatable element, a second reagent container containing a second detectable binding element that is specific for a first cell surface marker, wherein the first and second detectable binding elements are differentially detectable by the cytometer, and either a third reagent container containing a first modulator or a sample container containing a biological sample comprising cells, or both, wherein the modulator, the detectable binding elements, and the biological sample comprising cells are in liquid solution or suspension in their respective reagent containers;
  3. a dispensing head configured to withdraw liquid from one of said reagent or sample containers and dispense it to a well in said microplate, and/or to withdraw liquid from a first well in the microplate and dispense it to a second well in the same or different microplate;
  4. a microplate handling apparatus for moving said microplate, wherein:
    i. said microplate handling apparatus is configured to position said microplate near said dispensing head so that said dispensing head can dispense liquid from a reagent container into a well in said microplate and/or withdraw liquid from a well in said microplate during the production of a processed sample; and,
    ii. said microplate handling apparatus is configured to either relocate said microplate to said cytometer for transfer of the processed sample to, and analysis of the processed sample by, the cytometer, or to position said microplate so that it may be relocated manually to said cytometer for transfer of the processed sample to, and analysis of the processed sample by the cytometer;
  5. a heating and shaking instrument; and
  6. a tracking mechanism, wherein the tracking mechanism is automated, manual, or a combination thereof, and wherein the tracking mechanism comprises a barcode reader, a manual input station, or a combination thereof;
- b. providing a system for analysis and management of the processed samples in step a, comprising:
  1. said cytometer, wherein the cytometer is configured to differentially detect a plurality of differentially detectable binding elements bound to activable elements and cell surface markers in single cells present in said samples; and
  2. a computer system wherein said computer system comprises
    i. a processor,
    ii. a display unit,
    iii. a LIMS configured to track and record an experiment, inventory management and experimental design and to automate sample tracking from wherever the sample is initially input into the automation system through to data analysis and completion, and
    iv. a memory unit configured to control, and operably connected to, the microplate holder, said tracking mechanism, the microplate handling apparatus, the dispensing head, and the cytometer, wherein the memory unit and the LIMS are configured to communicate with the cytometer by instrument control and image processing application software to inform the cytometer as to plate layout, including the presence or absence of the first or second differentially detectable binding elements, or combination thereof, for each well in the plate, wherein there are potentially at least 6 differentially detectable binding elements and each well of the plate may contain one or more different binding elements compared to other wells, as well as the presence or absence of one or more modulators, with corresponding modulation time, so as to direct proper analysis of each of the samples in each well of the plate by the cytometer, in a manner compatible with the cytometer software, wherein the computer system is configured to consolidate elements of data or metadata to a single file;
- c. withdrawing and dispensing liquids from said reagent containers into one or more wells of the at least one microplate to perform a protocol, wherein said protocol comprises:
  1. either:
    i. providing the at least one microplate, one or more of whose wells contains biological sample comprising cells, and dispensing modulator from said third reagent container into the wells so that the modulator and the cells are in contact; or
    ii. providing the at least one microplate, one or more of whose wells contains a modulator and dispensing at least one biological sample comprising cells from said sample container into the wells so that the modulator and the cells are in contact; or
    iii. providing the at least one microplate and dispensing at least one biological sample from the sample container into one or more wells of the microplate and dispensing modulator from the third reagent container into one or more of the wells of the microplate, so that the modulator and the cells are in contact;
  2. determining an activation level of at least said first activatable element in single cells in said one or more samples, wherein said first activatable element is an element in a pathway that is modulated by the modulator, by said cytometer, wherein said activation level is determined by a process comprising contacting said at least one biological sample with the first detectable binding element which is specific to an activation state of said first activatable element, wherein said contacting comprises withdrawing the first detectable binding element from said first reagent container and dispensing said first detectable binding element to the well in the microplate containing said sample such that said first detectable binding element contacts the cells in said sample and binds to the first activatable element, if present, and detecting said bound first detectable binding element in said cells on a single cell basis in the cytometer; and
  3. determining a level of at least said first cell surface marker in said one or more samples on a single cell basis by said cytometer, wherein said first cell surface marker level is determined by a process comprising: contacting said at least one biological sample with the second detectable binding element which is specific to the first cell surface marker, wherein said contacting comprises: withdrawing said second detectable binding element from said second reagent container and dispensing said second detectable binding element to the well in the microplate containing said sample such that said second detectable binding element contacts the cells in said sample and binds to said first cell surface marker, if present, and detecting said bound second detectable binding element in said cells on a single cell basis in the cytometer.

* * * * *